United States Patent
Inukai et al.

(10) Patent No.: US 11,639,885 B2
(45) Date of Patent: May 2, 2023

(54) METHOD FOR ANALYZING DEGREE OF HYDROPHOBICITY OF POWDER, HIGHLY HYDROPHOBIZED COLORING PIGMENT, AND COSMETIC CONTAINING SAID COLORING PIGMENT

(71) Applicant: SHIN-ETSU CHEMICAL CO., LTD., Tokyo (JP)

(72) Inventors: Tetsuya Inukai, Annaka (JP); Mitsugu Saito, Annaka (JP); Tomoki Okawa, Annaka (JP); Masanao Kamei, Annaka (JP); Hiroyuki Moriya, Annaka (JP); Chihiro Hayakawa, Tokyo (JP); Hiroko Kikuchi, Tokyo (JP); Ryuichi Inaba, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 541 days.

(21) Appl. No.: 16/616,254

(22) PCT Filed: May 23, 2018

(86) PCT No.: PCT/JP2018/019807
§ 371 (c)(1),
(2) Date: Nov. 22, 2019

(87) PCT Pub. No.: WO2018/216722
PCT Pub. Date: Nov. 29, 2018

(65) Prior Publication Data
US 2020/0132579 A1 Apr. 30, 2020

(30) Foreign Application Priority Data

May 25, 2017 (JP) .............................. JP2017-103654
Sep. 26, 2017 (JP) .............................. JP2017-184723

(51) Int. Cl.
*G01N 13/00* (2006.01)
*G01N 33/00* (2006.01)
(Continued)

(52) U.S. Cl.
CPC ............... *G01N 13/00* (2013.01); *A61K 8/06* (2013.01); *A61K 8/29* (2013.01); *C09C 1/24* (2013.01);
(Continued)

(58) Field of Classification Search
CPC ....................... G01N 13/00; G01N 2033/0091
See application file for complete search history.

(56) References Cited

U.S. PATENT DOCUMENTS 5,467,659 A * 11/1995 Young .................... G01N 11/02
73/866
5,605,992 A 2/1997 Urashima et al.
(Continued)

FOREIGN PATENT DOCUMENTS

JP 7-196946 A 8/1995
JP 2719303 B2 2/1998
(Continued)

OTHER PUBLICATIONS

WO-2015064703-A1—English (Year: 2015).*
(Continued)

*Primary Examiner* — Daniel S Larkin
*Assistant Examiner* — Fatemeh Esfandiari Nia
(74) *Attorney, Agent, or Firm* — Birch, Stewart, Kolasch & Birch, LLP

(57) ABSTRACT

The present invention addresses the problem of evaluating the hydrophobicity of a powder. According to the present invention, a powder is charged into a mixed solvent composed of a lipophilic solvent and a hydrophilic solvent, the voltage rate R of the mixed solvent is measured at prede-
(Continued)

termined time intervals while adding a lipophilic solvent to the mixed solvent charged with the powder, a parameter x correlating with the concentration of powder is defined for an arbitrary voltage rate R, a continuous function HP(x) of the ratio of a lipophilic solvent corresponding to x is defined, and HP(x) for required x is set as a representative value of a lipophilic solvent ratio distribution and used as an index of hydrophobicity.

15 Claims, 3 Drawing Sheets

(51) Int. Cl.

| | | |
|---|---|---|
| *A61K 8/06* | (2006.01) | |
| *A61K 8/29* | (2006.01) | |
| *C09C 1/24* | (2006.01) | |
| *C09C 1/36* | (2006.01) | |
| *C09C 3/12* | (2006.01) | |
| *A61Q 1/06* | (2006.01) | |
| *A61Q 1/10* | (2006.01) | |
| *A61Q 1/12* | (2006.01) | |

(52) U.S. Cl.
CPC .................. *C09C 1/36* (2013.01); *C09C 3/12* (2013.01); *A61Q 1/06* (2013.01); *A61Q 1/10* (2013.01); *A61Q 1/12* (2013.01); *G01N 2033/0091* (2013.01)

(56) References Cited

U.S. PATENT DOCUMENTS

| | | | | |
|---|---|---|---|---|
| 10,684,222 B2* | 6/2020 | Horiuchi | ................ | G01N 21/51 |
| 2003/0162111 A1* | 8/2003 | Otani | ................ | G03G 9/09783 |
| | | | | 430/108.4 |
| 2004/0156809 A1* | 8/2004 | Ono | ................ | A61K 8/11 |
| | | | | 424/70.12 |
| 2004/0266926 A1* | 12/2004 | Sasaki | ................ | C08F 2/22 |
| | | | | 524/275 |
| 2007/0071980 A1* | 3/2007 | Kamei | ................ | A61K 8/27 |
| | | | | 428/405 |
| 2007/0207176 A1* | 9/2007 | Kamei | ................ | A61K 8/26 |
| | | | | 424/401 |
| 2010/0135938 A1* | 6/2010 | Ishikubo | ................ | A61Q 19/00 |
| | | | | 424/59 |
| 2016/0262991 A1 | 9/2016 | Akabane et al. | | |

FOREIGN PATENT DOCUMENTS

| | | | |
|---|---|---|---|
| JP | 2761188 B2 | 6/1998 | |
| JP | 2006-195025 A | 7/2006 | |
| JP | 2006-290712 A | 10/2006 | |
| JP | 2009300718 A | * 12/2009 | |
| JP | 2011-64868 A | 3/2011 | |
| JP | 5096802 B2 | 12/2012 | |
| JP | 2013-151436 A | 8/2013 | |
| JP | 2014-62135 A | 4/2014 | |
| JP | 5576055 B2 | 8/2014 | |
| JP | 2015-219347 A | 12/2015 | |
| JP | 5862848 B2 | 2/2016 | |
| JP | 2016-88935 A | 5/2016 | |
| JP | 5949698 B2 | 7/2016 | |
| JP | 2016-169324 A | 9/2016 | |
| JP | 2017-75319 A | 4/2017 | |
| WO | WO 2015/064703 A1 | 5/2015 | |
| WO | WO-2015064703 A1 | * 5/2015 | ............. C09B 17/02 |

OTHER PUBLICATIONS

JP-2009300718-A—English (Year: 2009).*
Japanese Notice of Reasons for Refusal for Japanese Application No. 2020-159355, dated May 10, 2022, with an English translation.
International Search Report, issued in PCT/JP2018/019807, dated Aug. 7, 2018.
Murota et al., "Effect of Alkyl Chain Length on the Reaction of Alkylalkoxysilane with Ultrafine Silica Particles in Dry System", Journal of the Japan Society of Colour Material, 2001, vol. 74, No. 4, pp. 178-184.
Noboru et al., "A New Instrument for the Measurement of Wettability of Hydrophobic Powders", Journal of Japan Coating Technology/ Association, 1997, vol. 32, No. 6, pp. 218-223.
Written Opinion of the International Searching Authority, issued in PCT/JP2018/019807, dated Aug. 7, 2018.
Li et al., "Wetting of Octadecylsilylated Silica in Methanol-Water Eluents," Anal. Chem. (1996), vol. 68, pp. 124-129.
Partial European Search Report dated Mar. 12, 2021, in European Patent Application No. 18806612.0.

* cited by examiner

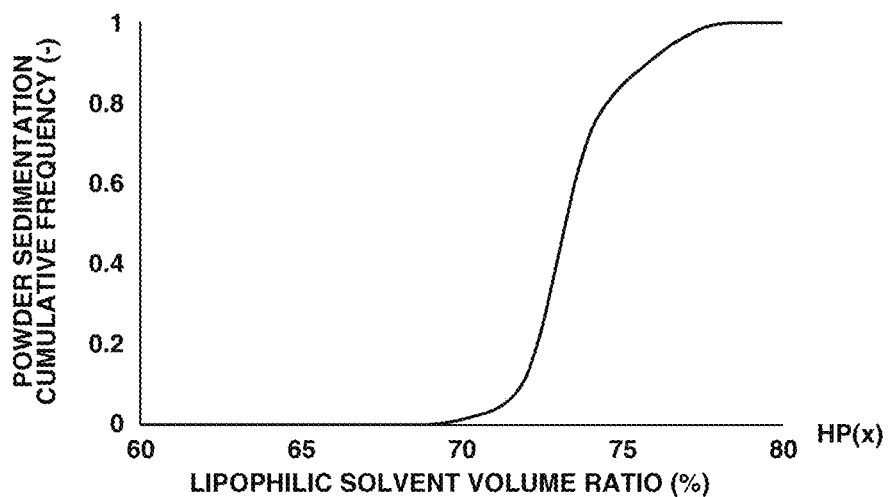

FIG.6

| | EXAMPLE 1 | REFERENCE EXAMPLE 1 | REFERENCE EXAMPLE 2 | EXAMPLE 4 | EXAMPLE 5 | EXAMPLE 6 |
|---|---|---|---|---|---|---|
| EVALUATION OF DISPERSION | | | | | | |
| RESULTS OF EVALUATION | ○ | △ | △ | ○ | ○ | ○ |

1

METHOD FOR ANALYZING DEGREE OF HYDROPHOBICITY OF POWDER, HIGHLY HYDROPHOBIZED COLORING PIGMENT, AND COSMETIC CONTAINING SAID COLORING PIGMENT

TECHNICAL FIELD

This invention relates to a method for analyzing the degree of hydrophobicity of a powder using a statistical index as a parameter for powder hydrophobicity, a pigment which is evaluated to have a high hydrophobic function in terms of a parameter computed by the analysis method, and a cosmetic composition comprising one or more highly hydrophobic pigments.

BACKGROUND ART

One known method for evaluating surface properties of powder is a method for measuring a degree of hydrophobicity by the methanol wettability (MW) test. The titration method is similarly discussed in technical reports and latest patents. For example, Non-Patent Document 1: Journal of the Japan Society of Colour Material, 74 [4], 178-184 (2001) includes the following description.
"The degree of hydrophobicity or methanol wettability (MW) of treated silica is determined by charging a 200-mL beaker with 50 mL of purified water and 0.2 g of treated silica, adding methanol thereto with stirring, measuring the volume of methanol titrated until the silica floating on the water surface settles down, and calculating MW according to Equation 1:

$$MW\ (\%) = A/(50+A) \times 100 \qquad (1)$$

wherein A is the volume (mL) of methanol added dropwise."

Also, Patent Document 1: JP 2761188 includes similar description. "As used herein, the index of hydrophobicity is a numerical value obtained by the following procedure.
A sample, 0.2 g, is weighed into a 200-mL beaker and 50 mL of purified water is added thereto.
With electromagnetic stirring, methanol is added below the water surface.
The point of time when the sample is no longer recognized on the water surface is the end of addition.
The degree of hydrophobicity is calculated from the volume of methanol added according to the following equation:

$$\text{Index of hydrophobicity } (\%) = [x/(50+x)] \times 100$$

wherein x is the volume (mL) of methanol used."

It is emphasized that the relationship of numerical values is definitely described under fixed conditions over decades. Among patents referring to the measurement method based on the methanol titration volume, many patents describe that the end point of settling is regarded as a measure for degree of hydrophobicity, for example, Patent Document 2: JP 5949698. Typical of the patent describing that the start point of settling in a similar measurement procedure is regarded as a measure for degree of hydrophobicity is Patent Document 3: JP 5576055. Most patent documents relating to the measurement method do not judge the index by the end point or start point, for example, Patent Document 4: JP 5096802. The patent document relating to the methanol titration method and utilizing the average value of the start point and the end point as a measure for degree of hydrophobicity is Patent Document 5: JP 5862848.
Non-Patent Document 2: Journal of Japan Coating Technology/Association, 32 [6], 218-223 (1997) proposes an apparatus for recognizing the process of a powder being suspended in a water/organic solvent mixture while continuously changing the water/organic solvent ratio, by utilizing a change of transmittance of laser light. The discussion is developed that the surface tension value of the solvent mixture read at the start point of suspension is correlated to the critical surface tension of the powder.

Patent Document 6: JP-A 2006-195025 and Patent Document 7: WO 2015/064703 describe the evaluation method using a powder wettability tester of Rhesca Co., Ltd. based on the measurement principle.

The powder which cannot be conveniently measured at the relevant concentration by the above methanol titration method must be addressed by an alternative method as will be described later. That is, in the case of the prior art analysis method wherein bits of information are obtained in the process of evaluating the hydrophobicity of a powder while suspending the powder in the solvent mixture and changing the ratio of organic solvent to hydrophilic solvent, the objective and quantitative evaluation of hydrophobicity was impossible because of ambiguous selection of information bits and an ambiguous index for selection.

Meanwhile, pigments such as iron oxide and titanium oxide are widely used in the field of cosmetics such as foundations, mascaras, eye liners and lipsticks. In general, these pigments are subjected to hydrophobic treatments such as metal soap treatment, alumina treatment, silicone treatment and phosphate treatment for imparting satisfactory water repellency and good dispersibility, before they are used in cosmetics.

For example, Patent Document 8: JP 2719303 discloses a method for surface treatment of 100 parts by weight of powder with 12 to 60 parts by weight of methylhydrogenpolysiloxane. Patent Document 9: JP-A H07-196946 discloses a surface treatment method using a linear single end alkoxy-modified silicone.

The treatment for rendering the surface of a pigment hydrophobic is a well-known technique. In the case of coloring pigments, the treated state of pigments is poor. If a coloring pigment which has not been treated fully hydrophobic is formulated in a cosmetic composition, the pigment will agglomerate together in the cosmetic composition. Then a color separation phenomenon occurs due to sedimentation or separation. The cosmetic composition is exacerbated in stability with time, leading to a loss of aesthetic effect and a drop of commercial value.

If the amount of a surfactant blended is increased in order to prevent the agglomeration and to improve the dispersion of a pigment, it gives rise to a problem of feel-on-use such as a heavy and greasy feel-on-use. Such a phenomenon frequently occurs with emulsion type cosmetics such as cream foundations and liquid foundations.

As discussed above, the quality and stability of cosmetic compositions are substantially governed by the accuracy of hydrophobic treatment of pigments. There is the demand for a method capable of measuring the degree of hydrophobicity of various coloring pigments, which enables easy selection of a surface-treated coloring pigment having a high degree of hydrophobicity.

PRIOR ART DOCUMENTS

Patent Documents

Patent Document 1: JP 2761188
Patent Document 2: JP 5949698
Patent Document 3: JP 5576055

Patent Document 4: JP 5096802
Patent Document 5: JP 5862848
Patent Document 6: JP-A 2006-195025
Patent Document 7: WO 2015/064703
Patent Document 8: JP 2719303
Patent Document 9: JP-A H07-196946

Non-Patent Documents

Non-Patent Document 1: Journal of the Japan Society of Colour Material, 74 [4], 178-184 (2001)
Non-Patent Document 2: Journal of Japan Coating Technology/Association, 32 [6], 218-223 (1997)

SUMMARY OF INVENTION

Technical Problem

Addressing the problem of the prior art technique wherein bits of information are obtained in the process of evaluating the hydrophobicity of a powder while changing the ratio of organic solvent to hydrophilic solvent and suspending the powder in the solvent mixture, but selection of information bits and an index for selection are ambiguous, an object of the invention is to provide an analysis method using as a parameter for evaluating the hydrophobicity of a powder, a statistical index correlating to a cumulative sedimentation weight of powder which is a physical/chemical statistic.

Another object of the invention is to provide a cosmetic composition comprising a highly hydrophobized pigment such as a surface-treated coloring pigment which is evaluated as having a high hydrophobicity function by using the statistical index computed by the above analysis method as the parameter, the cosmetic composition having excellent stability with time and feel-on-use without losing the desired aesthetic effect because the pigment does not agglomerate therein and no color separation occurs.

Solution to Problem

Making extensive investigations to attain the above object, the inventors have found, among the results obtained by measuring a change with time of a light transmittance while continuously changing a ratio of lipophilic solvent to hydrophilic solvent, and suspending a powder to be evaluated for its degree of hydrophobicity in the solvent mixture, an analysis method for obtaining a statistical index of hydrophobicity representing that a statistical variation of the hydrophobic state at the powder surface is reflected by a dispersion concentration in the solvent.

The inventors have also found a surface-treated coloring pigment which is evaluated as having a high hydrophobicity function in terms of hydrophobicity parameter HP(x) obtained by the analysis method of the invention.

Further it has been found that a cosmetic composition comprising the surface-treated coloring pigment, especially silicone surface-treated coloring pigment is effective for preventing quality spoiling and optical degradation, and exhibits stability with time and excellent feel-on-use without the loss of aesthetic effect. The invention is predicated on this finding.

Accordingly, the invention provides a method for analyzing the degree of hydrophobicity of a powder, a high-hydrophobicity-treated coloring pigment, and a cosmetic composition, as defined below.

[1] A method for analyzing the degree of hydrophobicity of a powder, comprising the steps of:
adding a powder to be evaluated for its degree of hydrophobicity to a solvent mixture of a lipophilic solvent and a hydrophilic solvent,
continuously adding the lipophilic solvent to the solvent mixture having the powder added thereto,
measuring a voltage rate of the solvent mixture at predetermined time intervals, at least until the voltage rate reaches the minimum,
provided that for data discrete values as measured, the voltage rate observed relative to time series $t_i$ (wherein i is an integer, $t_i < t_{i+1}$) is $R_i$, the maximum of voltage rate is 100, and the minimum of voltage rate is $R_{min}$, a parameter correlating to a powder concentration relative to an arbitrary voltage rate R in the range: $R_{min} < R < 100$ is defined as

[Math. 1]
$$X = \frac{100 - R}{100 - R_{min}} \times 100 \text{(wherein } 0 < x < 100\text{)},$$

a lipophilic solvent ratio in the solvent mixture corresponding to that x is represented by HP(x), a continuous function HP(x) of lipophilic solvent ratio is defined, for R meeting the range: $R_{i+1} \leq R < R_i$ wherein i is an integer, as

[Math. 2]
$$HP(x) = \frac{HP_{i+1} - HP_i}{R_{i+1} - R_i} \times (R - R_i) + HP_i,$$

and the parameter x (wherein 0<x<100) changes in proportion to a powder concentration c(t) (wherein $0 < c(t) < c_{max}$) or cumulative sedimentation weight W(t) (wherein $0 < W(t) < W_{max}$), computing HP(x) at a preselected value of x as a representative value of the lipophilic solvent ratio distribution, the HP(x) being regarded as an index of hydrophobicity.

[2] The analysis method of [1] wherein for the voltage rate $R_i$ observed relative to time series $t_i$, measurement data at total (2n+1) points (wherein n is an integer) including a certain point and fore and aft n points are averaged, a value obtained by smoothening according to the equation:

[Math. 3]
$$\overline{R_i} = \sum_{i=-n}^{n} R_i$$

is used as the voltage rate, the maximum of voltage rate is 100, and the minimum of averaged voltage rate is $$\overline{R_{min}},$$ [Math. 4]

a parameter correlating to a powder concentration with respect to an arbitrary voltage rate R in the range:

$$\overline{R_{min}} < R < 100$$ [Math. 5]

is defined as

[Math. 6]
$$x = \frac{100 - R}{100 - \overline{R_{min}}} \times 100 \text{(wherein } 0 < x < 100\text{)},$$

a lipophilic solvent ratio corresponding to that x is represented by HP(x), for R meeting the range:

$$\overline{R_{i+1}} \leq R < \overline{R_i} \quad [\text{Math. 7}]$$

a continuous function HP(x) of lipophilic solvent ratio is defined as $$HP(x) = \frac{HP_{i+1} - HP_i}{\overline{R_{i+1}} - \overline{R_i}} \times (R - \overline{R_i}) + HP_i. \quad [\text{Math. 8}]$$

[3] The analysis method of [1] or [2] wherein HP(50) is computed as a representative value of the lipophilic solvent ratio distribution.

[4] The analysis method of any one of [1] to [3] wherein the lipophilic solvent is at least one solvent selected from methanol, ethanol, isopropyl alcohol, butyl alcohol, and acetone, and the hydrophilic solvent is water.

[5] The analysis method of [3] wherein when the lipophilic solvent is methanol and the hydrophilic solvent is water, a powder having a parameter HP(50) meeting 68.0≤HP(50) is evaluated as having a high degree of hydrophobicity.

[6] The analysis method of [5] wherein when HP(10) and HP(90) are further computed, and HP(90)-HP(10) is used as an index for variation of the lipophilic solvent ratio, a powder meeting HP(90)-HP(10)≤22.0 is evaluated as having a small variation.

[7] The analysis method of [3] wherein when the lipophilic solvent is ethanol and the hydrophilic solvent is water, a powder having a parameter HP(50) meeting 30.0≤HP(50) is evaluated as having a high degree of hydrophobicity.

[8] The analysis method of [7] wherein when HP(10) and HP(90) are further computed, and HP(90)-HP(10) is used as an index for variation of the lipophilic solvent ratio, a powder meeting HP(90)-HP(10)≤28.0 is evaluated as having a small variation.

[9] A high-hydrophobicity-treated coloring pigment comprising a coloring pigment which has been subjected to hydrophobic surface treatment and meets 68.0≤HP(50) as analyzed by the method of [5].

[10] A high-hydrophobicity-treated coloring pigment comprising a coloring pigment which has been subjected to hydrophobic surface treatment and meets 68.0≤HP(50) and HP(90)-HP(10)≤22.0 as analyzed by the method of [6].

[11] A high-hydrophobicity-treated coloring pigment comprising an inorganic pigment which has been subjected to hydrophobic surface treatment, wherein the inorganic pigment is a red iron oxide pigment meeting 68.0≤HP(50),
a yellow iron oxide pigment meeting 68.0≤HP(50),
a white titanium oxide pigment meeting 73.0≤HP(50), or
a black iron oxide pigment meeting 72.5≤HP(50),
as analyzed by the method of [5].

[12] A high-hydrophobicity-treated coloring pigment comprising an inorganic pigment which has been subjected to hydrophobic surface treatment, wherein the inorganic pigment is a red iron oxide pigment meeting 68.0≤HP(50) and HP(90)-HP(10)≤16.0,
a yellow iron oxide pigment meeting 68.0≤HP(50) and HP(90)-HP(10)≤22.0,
a white titanium oxide pigment meeting 73.0≤HP(50) and HP(90)-HP(10)≤20.0, or
a black iron oxide pigment meeting 72.5≤HP(50) and HP(90)-HP(10)≤9.0,
as analyzed by the method of [6].

[13] A high-hydrophobicity-treated coloring pigment comprising a coloring pigment which has been subjected to hydrophobic surface treatment and meets 30.0≤HP(50) as analyzed by the method of [7].

[14] A high-hydrophobicity-treated coloring pigment comprising a coloring pigment which has been subjected to hydrophobic surface treatment and meets 30.0≤HP(50) and HP(90)-HP(10)≤28.0 as analyzed by the method of [8].

[15] A high-hydrophobicity-treated coloring pigment comprising an inorganic pigment which has been subjected to hydrophobic surface treatment, wherein the inorganic pigment is a red iron oxide pigment meeting 30.0≤HP(50),
a yellow iron oxide pigment meeting 30.0≤HP(50),
a white titanium oxide pigment meeting 36.0≤HP(50), or
a black iron oxide pigment meeting 40.0≤HP(50),
as analyzed by the method of [7].

[16] A high-hydrophobicity-treated coloring pigment comprising an inorganic pigment which has been subjected to hydrophobic surface treatment, wherein the inorganic pigment is a red iron oxide pigment meeting 30.0≤HP(50) and HP(90)-HP(10)≤18.0,
a yellow iron oxide pigment meeting 30.0≤HP(50) and HP(90)-HP(10)≤21.0,
a white titanium oxide pigment meeting 36.0≤HP(50) and HP(90)-HP(10)≤19.0, or
a black iron oxide pigment meeting 40.0≤HP(50) and HP(90)-HP(10)≤18.0,
as analyzed by the method of [8].

[17] The high-hydrophobicity-treated coloring pigment of any one of [9] to [16] wherein at least one treating agent used for the hydrophobic surface treatment is a silicone compound.

[18] The high-hydrophobicity-treated coloring pigment of [17] wherein at least one silicone compound used for the hydrophobic surface treatment is triethoxysilylethyl polydimethylsiloxyethylhexyl dimethicone.

[19] The high-hydrophobicity-treated coloring pigment of any one of [9] to [18], having a volume average particle size of 150 to 600 nm.

[20] A method for evaluating a hydrophobic-treated pigment comprising analyzing a coloring pigment which has been subjected to hydrophobic surface treatment by the hydrophobicity analysis method of [5], a pigment meeting 68.0≤HP(50) being evaluated as having a high degree of hydrophobicity.

[21] A method for evaluating a hydrophobic-treated pigment comprising analyzing an inorganic pigment which has been subjected to hydrophobic surface treatment by the hydrophobicity analysis method of [5], a red iron oxide pigment meeting 68.0≤HP(50),
a yellow iron oxide pigment meeting 68.0≤HP(50),
a white titanium oxide pigment meeting 73.0≤HP(50) or
a black iron oxide pigment meeting 72.5≤HP(50),
being evaluated as having a high degree of hydrophobicity.

[22] A method for evaluating a hydrophobic-treated pigment comprising analyzing an inorganic pigment which has been subjected to hydrophobic surface treatment by the hydrophobicity analysis method of [6], a red iron oxide pigment meeting 68.0≤HP(50) and HP(90)-HP(10)≤16.0,
a yellow iron oxide pigment meeting 68.0≤HP(50) and HP(90)-HP(10)≤22.0,
a white titanium oxide pigment meeting 73.0≤HP(50) and HP(90)-HP(10)≤20.0 or a black iron oxide pigment meeting 72.5≤HP(50) and HP(90)-HP(10)≤9.0,
being evaluated as having a small variation and a high degree of hydrophobicity.

[23] A method for evaluating a hydrophobic-treated pigment comprising analyzing a coloring pigment which has been subjected to hydrophobic surface treatment by the hydrophobicity analysis method of [7], a pigment meeting 30.0≤HP(50) being evaluated as having a high degree of hydrophobicity.

[24] A method for evaluating a hydrophobic-treated pigment comprising analyzing an inorganic pigment which has been subjected to hydrophobic surface treatment by the hydrophobicity analysis method of [7],
a red iron oxide pigment meeting 30.0≤HP(50),
a yellow iron oxide pigment meeting 30.0≤HP(50),
a white titanium oxide pigment meeting 36.0≤HP(50) or
a black iron oxide pigment meeting 40.0≤HP(50),
being evaluated as having a high degree of hydrophobicity.

[25] A method for evaluating a hydrophobic-treated pigment comprising analyzing an inorganic pigment which has been subjected to hydrophobic surface treatment by the hydrophobicity analysis method of [8],
a red iron oxide pigment meeting 30.0≤HP(50) and HP(90)-HP(10)≤18.0,
a yellow iron oxide pigment meeting 30.0≤HP(50) and HP(90)-HP(10)≤21.0,
a white titanium oxide pigment meeting 36.0≤HP(50) and HP(90)-HP(10)≤19.0 or
a black iron oxide pigment meeting 40.0≤HP(50) and HP(90)-HP(10)≤18.0,
being evaluated as having a small variation and a high degree of hydrophobicity.

[26] The evaluating method of any one of [20] to [25] wherein the hydrophobic surface treatment is a surface treatment with a silicone compound as at least one treating agent.

[27] A cosmetic composition comprising at least one high-hydrophobicity-treated coloring pigment of any one of [9] to [19].

[28] The cosmetic composition of [27] which is in the form of an emulsion.

Advantageous Effects of Invention

The analysis method of the invention enables easy selection of a highly hydrophobic pigment, typically a surface-treated coloring pigment exerting a highly hydrophobic function. When a pigment having a hydrophobicity parameter HP(x) in the range: 68.0≤HP(50), especially a surface-treated coloring pigment meeting 68.0≤HP(50) and HP(90)-HP(10)≤22.0, as analyzed by the analysis method of the invention using methanol as the lipophilic solvent and water as the hydrophilic solvent, or a surface-treated coloring pigment having a hydrophobicity parameter HP(x) in the range: 30.0≤HP(50), especially 30.0≤HP(50) and HP(90)-HP(10)≤28.0, as analyzed by the analysis method of the invention using ethanol as the lipophilic solvent and water as the hydrophilic solvent is formulated in a cosmetic composition, the pigment is kept fully dispersed in the cosmetic composition without agglomerating together.

In particular, a versatile coloring pigment, especially red iron oxide pigment, yellow iron oxide pigment, white titanium oxide pigment or black iron oxide pigment is selected. When a pigment having the following values of hydrophobicity parameter HP(x), specifically
a red iron oxide pigment meeting 68.0≤HP(50) and HP(90)-HP(10)≤16.0,
a yellow iron oxide pigment meeting 68.0≤HP(50) and HP(90)-HP(10)≤22.0,
a white titanium oxide pigment meeting 73.0≤HP(50) and HP(90)-HP(10)≤20.0, or
a black iron oxide pigment meeting 72.5≤HP(50) and HP(90)-HP(10)≤9.0,
as analyzed by the analysis method of the invention using methanol as the lipophilic solvent and water as the hydrophilic solvent, is formulated in a cosmetic composition; or when a pigment having the following values of hydrophobicity parameter HP(x), specifically
a red iron oxide pigment meeting 30.0≤HP(50) and HP(90)-HP(10)≤18.0,
a yellow iron oxide pigment meeting 30.0≤HP(50) and HP(90)-HP(10)≤21.0,
a white titanium oxide pigment meeting 36.0≤HP(50) and HP(90)-HP(10)≤19.0, or
a black iron oxide pigment meeting 40.0≤HP(50) and HP(90)-HP(10)≤18.0,
as analyzed by the analysis method of the invention using ethanol as the lipophilic solvent and water as the hydrophilic solvent, is formulated in a cosmetic composition, the coloring pigment is kept fully dispersed in the cosmetic composition without agglomerating together. Accordingly, neither sedimentation of the coloring pigment nor color separation occurs. There is provided a cosmetic composition having excellent aesthetic effect, stability with time, and feel-on-use.

BRIEF DESCRIPTION OF DRAWINGS

FIG. 3 is a graph showing the relationship of powder sedimentation cumulative frequency to a lipophilic solvent volume ratio HP(x).

FIG. 4 illustrates the results of the evaluation of dispersion of Examples 1, 2 and Reference Examples 1, 2 in Test 1.

FIG. 5 illustrates the results of the evaluation of dispersion of Example 3 and Reference Examples 3, 4 in Test 4.

FIG. 6 illustrates the results of the evaluation of dispersion of Examples 1, 4 to 6 and Reference Examples 1, 2 in Test 5.

DESCRIPTION OF EMBODIMENTS

[Analysis Method]

Figure 1:
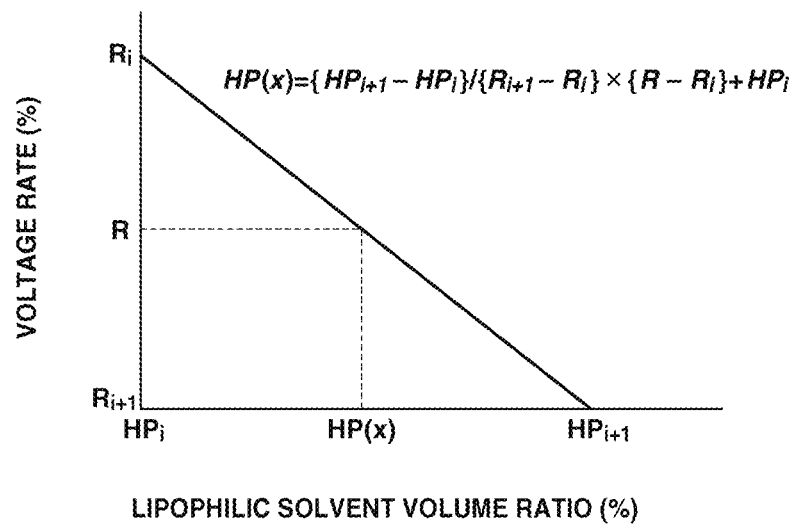
FIG. 1 is a graph showing the relationship $HP(x)=(HP_{i+1}-HP_i)/(R_{i+1}-R_i)\times(R-R_i)+HP_i$ of a voltage rate $R_i$, $R$ and $R_{i+1}$ to a lipophilic solvent volume ratio $HP_i<HP(x)<HP_{i+1}$.

The solution means of the invention includes three stages. In the first stage, it is necessary to devise a parameter for evaluating hydrophobicity as a statistical index having taken into account variations associated with complex phenomena including a complex surface state and particle size distribution of a powder, powder surface wetting and sedimentation, and stirring/mixing. The second stage is to optimize the surface treatment process with a high-functionality polymer for improving the surface hydrophobicity of a pigment powder. As a result of extensive investigation, a surface-treated coloring pigment which exerts an outstandingly high hydrophobizing function which is never achieved in the prior art is found. At the third stage, there is found a cosmetic composition comprising the treated coloring pigment having a high hydrophobicity, having features not found in the prior art and a good overall balance.

These solutions are described in detail.

Referring to the invention, the measurement principle using continuous variables and the analysis model according to the invention are mainly described. Then, the method of analyzing measurement data as discrete variables is described.

1. Measurement Principle

The following is assumed. In the process of measuring a change with time of light transmittance while continuously changing a ratio of lipophilic solvent to hydrophilic solvent, and suspending a powder in the solvent mixture, light having a luminous flux $I_0$ passes through the solvent mixture having an optical path length X, powder concentration c, light scattering coefficient S, and light absorbing coefficient K, after which the luminous flux changes to I. Also, x-axis is set in the traveling direction of luminous flux and the coordinate origin is positioned where the luminous flux enters the solvent mixture. Light entering a thin layer of the liquid having a thickness dx in the traveling direction has a luminous flux i and light entering in the reverse direction has a luminous flux j.

[Math. 9]

$$\frac{di}{dx} = -(cS+cK)i + cSj \quad (1)$$

$$-\frac{dj}{dx} = -(cS+cK)j + cSi \quad (2)$$

Differentiation of (1) gives equation (3).

$$\frac{d^2 i}{dx^2} = -(cS+cK)\frac{di}{dx} + cS\frac{dj}{dx} \quad (3)$$

Substitution of (1) and (2) into (3) gives equation (4).

$$\frac{d^2 i}{dx^2} = c^2(2SK+K^2)i \quad (4)$$

Since $$\frac{di}{dx} < 0,$$

equation (5) is given.

$$\frac{di}{dx} = \left(-c\sqrt{2SK+K^2}\right)i \quad (5)$$

After equation (5) is subjected to separation of variables, integration of i from $I_0$ to I and of x from 0 to x gives the following.

$$\int_{I_0}^{I} \frac{di}{i} = \left(-c\sqrt{2SK+K^2}\right)\int_0^X dx \Leftrightarrow \ln i \Big|_{I_0}^{I} =$$

$$\left(-c\sqrt{2SK+K^2}\right)x\Big|_0^X \Leftrightarrow \frac{I}{I_0} = \exp\left(-cX\sqrt{2SK+K^2}\right)$$

Therefore, $$I = I_0 \exp(-cX\sqrt{2SK+K^2}) \quad (6)$$

Using a photovoltaic detector, output voltage E is given as $$E = A \ln I = A \ln I_0 - AcX\sqrt{2SK+K^2} \text{ (wherein } A \text{ is a constant)} \quad (7).$$

The output voltage decreases in linear proportion to a suspended powder concentration C.

2. Analysis Model According to Invention

Using measurement principle 1, the process of measuring a change with time of light transmittance while continuously changing a ratio of lipophilic solvent to hydrophilic solvent, and suspending a powder in the solvent mixture is described. Provided that t is measurement time, $V_M(t)$ is a lipophilic solvent volume, and $V_W$ is a hydrophilic solvent volume, then the total solvent volume is $V(t) = V_M(t) + V_W$.

Provided that W(t) is the cumulative weight of suspended powder, and $W_{max}$ is the weight of powder admitted, then the range of W(t) is $0 < W(t) < W_{max}$.

It is provided that the concentration of suspended powder is $$c(t) (= W(t)/V(t) = W(t)/[V_M(t)+V_W]),$$

the intensity of light transmitted by a sample is I(t),
the voltage is E(t) (=A ln I(t) wherein A is a constant),
the intensity of light when the powder is not suspended is $I_0$,
the voltage proportional thereto is $E_0$ (=A ln $I_0$),
the voltage rate is R(t) (=[E(t)/$E_0$]×100,
the minimum of voltage is $E_{min}$,
the minimum of voltage rate is $R_{min}$ (=[$E_{min}$/$E_0$]×100,
the time when the voltage reaches $E_{min}$ (voltage rate reaches $R_{min}$) is $t_{min}$,
that is, E($t_{min}$) = $E_{min}$ and
R($t_{min}$) = $R_{min}$,
the powder concentration at that point of time is c($t_{min}$).
A model giving the following is considered.

[Math. 10]

$$\frac{dc(t)}{dt} > 0 \quad \text{in the range } 0 < t < t_{min},$$

$$\lim_{t \to t_{min}} \frac{dc(t)}{dt} = 0 \quad \text{at } t = t_{min},$$

$$\frac{dc(t)}{dt} < 0 \quad \text{in the range } t_{min} < t, \text{ and}$$

$$c(t_{min}) = W(t_{min})/V(t_{min}) = W_{max}/(V_M(t_{min}) + V_W).$$

The lipophilic solvent volume ratio hp(t) is defined as $$\text{hp}(t) = [V_M(t)/\{V_M(t)+V_W\}] \times 100,$$

that is, lipophilic solvent volume ratio=[lipophilic solvent volume/(lipophilic solvent volume+hydrophilic solvent volume)]×100.

Since hp(t) shows a monotone increase relative to $V_M(t)$, and $V_M(t)$ shows a monotone increase relative to t, hp(t) increases monotone relative to time t.

Now the case where changes of light scattering coefficient and light absorbing coefficient are minute is considered, and an application of the case is intended. Since c(t)=0 and E(0)=$E_0$ in case of t=0, if the following:

[Math. 11]

$$E(t) = E_0 - Ac(t)X\sqrt{2SK+K^2} = E_0 - A\frac{W(t)}{V(t)}X\sqrt{2SK+K^2}$$

$$\angle E(t) \equiv E_0 - E(t)$$

is derived from equation (7),
then $\triangle E(t) = E_0 - E(t) = Ac(t) X \sqrt{2SK+K^2}$
and if $\triangle E_{max} \equiv E_0 - E_{min}$,
then $\triangle E_{max} = E_0 - E_{min} = Ac(t_{min}) X \sqrt{2SK+K^2}$.
Therefore, $$\frac{\triangle E(t)}{\triangle E_{max}} = \frac{E_0 - E(t)}{E_0 - E_{min}} = \frac{c(t)}{c(t_{min})} = \frac{W(t)}{W_{max}} \frac{V(t_{min})}{V(t)}. \quad (8)$$

Since $$\frac{dc(t)}{dt} > 0$$

in the range: $0 < t < t_{min}$, i.e., $0 < W(t) < W_{max}$, the following:

$$\frac{d}{dt}\left(\frac{\triangle E(t)}{\triangle E_{max}}\right) = \frac{d}{dt}\left[\frac{W(t)}{W_{max}} \frac{V(t_{min})}{V(t)}\right] = \frac{V(t_{min})}{W_{max}} \frac{d}{dt}\left[\frac{W(t)}{V(t)}\right] = \frac{V(t_{min})}{W_{max} V(t)} \frac{dc(t)}{dt} > 0$$

is derived.
Since $$\frac{dW(t)}{dt} = 0$$

in the range: $t_{min} \leq t$, i.e., $W(t) = W_{max}$, the following:

$$\frac{d}{dt}\left(\frac{\triangle E(t)}{\triangle E_{max}}\right) = \frac{d}{dt}\left[\frac{V(t_{min})}{V(t)}\right] = V(t_{min})\frac{d}{dt}\left[\frac{1}{V(t)}\right] = V(t_{min}) \cdot \left[-\frac{1}{V(t)^2} \frac{dV(t)}{dt}\right] < 0$$

is derived.
Therefore, $$\frac{\triangle E(t)}{\triangle E_{max}}$$

shows a monotone increase at $0 < t < t_{min}$, and changes within the range:

$$0 < \frac{\triangle E(t)}{\triangle E_{max}} < 1.$$

Similarly with respect to the voltage rate,
if $\Delta R(t) \equiv 100 - R(t)$ and
$\Delta R_{max} \equiv 100 - R_{min}$,
then the following is derived.

[Math. 12]

$$\frac{\triangle R(t)}{\triangle R_{max}} = \frac{100 - R(t)}{100 - R_{min}} = \frac{100 - \frac{E(t)}{E_0} \times 100}{100 - \frac{E_{min}}{E_0} \times 100} = \frac{E_0 - E(t)}{E_0 - E_{min}} = \frac{\triangle E(t)}{\triangle E_{max}}$$

Hence, x is defined by the following equation:

$$x \equiv \frac{\triangle E(t)}{\triangle E_{max}} \times 100 = \frac{\triangle R(t)}{\triangle R_{max}} \times 100$$

in the range: $0 < t \leq t_{min}$, then x shows a monotone increase at $0 < t < t_{min}$, and changes within the range: $0 < x < 100$.
Also, the following:

[Math. 13]

$$x \propto \frac{W(t)}{W_{max}}$$

is derived from equation (8), then x is a variable having the meaning that it correlates to a relative ratio of suspended cumulative sedimentation weight.

Based on the foregoing, in a continuous interval of the lipophilic solvent volume ratio hp(t),
(i) the weight of powder admitted is adjusted so as to meet $E_{min} > 0$ or $R_{min} > 0$, and the measuring time is $t > t_{min}$,
(ii) a change with time of voltage E(t) or voltage rate R(t) is measured,
(iii) the difference between the maximum $E_0$ and the minimum $E_{min}$ of voltage or the difference between the maximum 100 and the minimum $R_{min}$ of voltage rate R is determined, from which a quantity correlating to the maximum of the powder concentration (or powder weight) in the solvent, $E_0 - E_{min}$ or $100 - R_{min}$ is computed,
(iv) the difference between the maximum $E_0$ of voltage and the voltage E(t) or the difference between the maximum 100 of voltage rate R and the voltage rate R(t) is determined, from which a quantity correlating to the cumulative value of the powder concentration or powder weight in the solvent, $E_0 - E(t)$ or $100 - R(t)$ is computed,
(v) the cumulative value-correlating quantity obtained in (iv) is divided by the maximum value-correlating quantity obtained in (iii), whereby a quantity correlating to the relative cumulative value of the powder concentration or powder weight in the solvent is computed:

$([E_0 - E(t)]/[E_0 - E_{min}]) \times 100$ or $([100 - R(t)]/[100 - R_{min}]) \times 100$, (vi) x as a function of t is defined by the following equation:

$x = ([E_0 - E(t)]/[E_0 - E_{min}]) \times 100$ or $x = ([100 - R(0)]/[100 - R_{min}]) \times 100$, with the proviso $0 < t < t_{min}$ and $0 < x < 100$,
the inverse function of $y = E(z)$ is represented by $z = E^{-1}(y)$, t is represented as a function of x by the following equation:

$t = E^{-1}(E_{0-x} \times [E_0 - E_{min}]/100)$ or $t = R^{-1}(100 - x \times [100 - R_{min}]/100)$ this t is substituted into hp(t), giving:

$hp(0) = hp(E^{-1}(E_{0-x} \times [E_0 - E_{min}]/100)) \equiv HP(x)$ or $hp(0) = hp(R^{-1}(100 - x \times [100 - R_{min}]/100)) \equiv HP(x)$, that is, HP(x) is computed after the variable of lipophilic solvent volume ratio is converted to x,
(vii) the correlation quantity x correlating to the relative cumulative value $W(t)/W_{max}$ of the powder concentration or powder weight in the solvent is a cumulative frequency, and a relative cumulative distribution of lipophilic solvent volume ratio as a variable:

$HP(x)$ and $0<x<100$ is used as an index of hydrophobicity, or
a plurality of lipophilic solvent volume ratio $HP(\alpha_j)$ having values $\alpha_j$ (wherein $0<\alpha_j<100$, j is an integer) substituted into x of $HP(x)$ are representative values of the distribution, and $HP(\beta)-HP(\alpha)$ relating to $\alpha$ and $\beta$ meeting $0<\alpha<\beta<100$ is a variation of the distribution, giving as an index of hydrophobicity.

Then, hydrophobicity can be evaluated in an objective and quantitative manner by the index reflecting the statistical distribution on the powder surface.

3. Analysis of Discrete Variable Group

Based on the foregoing, the method for analyzing the degree of hydrophobicity of a powder according to the invention is described in detail.

First, a solvent mixture of a lipophilic solvent and a hydrophilic solvent is prepared. A powder to be evaluated for its degree of hydrophobicity is added to the solvent mixture. Although the lipophilic solvent volume ratio in the solvent mixture of lipophilic solvent and hydrophilic solvent varies depending on the identity of a powder to be evaluated for its hydrophobicity, measurement is possible when the lipophilic solvent volume ratio (%) is such that the powder to be evaluated for its hydrophobicity is not dispersed in the solvent mixture, but kept afloat on the solvent mixture. Typically, the solvent mixture prior to powder admission is prepared so that the lipophilic solvent volume ratio is 10 to 70% by volume, especially 60 to 70% by volume. The amount of the powder to be evaluated for its hydrophobicity admitted may be 0.01 to 0.30 g, preferably 0.01 to 0.20 g, more preferably 0.01 to 0.10 g per 300 mL (volume) of the solvent mixture.

While the lipophilic solvent is continuously added to the solvent mixture having added thereto the powder to be evaluated for its hydrophobicity, with stirring, the voltage rate of the solvent mixture having the powder dispersed therein is measured at predetermined time intervals. In this step, the stirring speed is preferably 10 to 600 rpm. The addition rate of the lipophilic solvent is preferably 1 to 10 mL/min, especially 5 to 10 mL/min, per 300 mL (volume) of the solvent mixture.

The measurement of voltage rate may be made at any suitable intervals, preferably at intervals of 0.01 to 10 seconds, more preferably 0.01 to 1 second, even more preferably 0.01 to 0.10 second. For the measurement of voltage rate, a well-known tester, for example, wettability tester WET1001 by Rhesca Co., Ltd. may be used.

In this step, the voltage rate is measured at least until the voltage rate reaches the minimum.

It is now assumed that for data discrete values as measured, the voltage rate observed relative to time series $t_i$ (wherein i is an integer, $t_i<t_{i+1}$) is $R_i$, and the corresponding lipophilic solvent volume ratio is $HP_i$. Since the voltage rate generates noises due to variations upon pump transportation or the like, it is not always likely that the voltage rate shows a monotone change relative to the time and the lipophilic solvent volume ratio like the analysis principle. It is thus preferable to carry out noise reduction on the voltage rate data. To this end, an approach of removing low-frequency fractions by Fourier transformation, or an approach of reducing noise influence by taking fore-and-aft average may be used. Referring to the latter approach, the voltage rate is averaged by taking an average of measurement data at total (2n+1) points including a certain point and fore and aft n points, thereby reducing the noise influence. That is, a value obtained by smoothening according to the calculation formula:

[Math. 14]

$$\overline{R_i} = \sum_{i=-n}^{n} R_i \text{ wherein } n \text{ is an integer}$$

is used as the voltage rate. If the maximum of voltage rate is 100, and the minimum of averaged voltage rate is $$\overline{R_{min}},$$ [Math. 15]

a parameter correlating to a powder concentration with respect to an arbitrary voltage rate R in the range:

$$\overline{R_{min}}<R<100$$ [Math. 16]

is defined as

[Math. 17]

$$x = \frac{100-R}{100-\overline{R_{min}}} \times 100 \text{ (wherein } 0 < x < 100\text{)},$$

and a lipophilic solvent ratio corresponding to that x is represented by $HP(x)$.
For R meeting the range:

$$\overline{R_{i+1}} \leq R < \overline{R_i},$$ [Math. 18]

a continuous function $HP(x)$ of lipophilic solvent ratio is defined by:

[Math. 19]

$$HP(x) = \frac{HP_{i+1} - HP_i}{\overline{R_{i+1}} - \overline{R_i}} \times (R - \overline{R_i}) + HP_i$$

Figure 2:
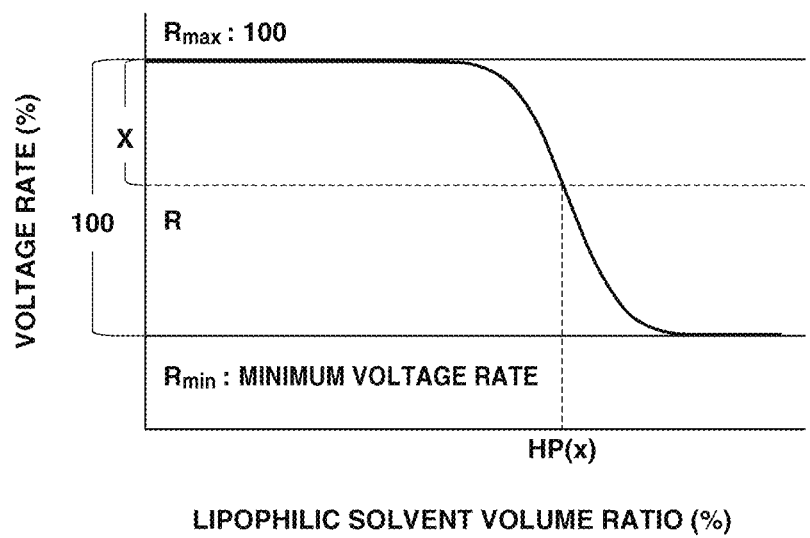
FIG. 2 is a graph showing the relationship of voltage rate to a lipophilic solvent volume ratio HP(x).

(see FIG. 1). Then a distribution function of lipophilic solvent ratio is obtainable with respect to a parameter x ($0<x<100$) which changes in proportion to a suspended powder concentration $c(t)$ ($0<c(t)<c_{max}$) or cumulative sedimentation weight $W(t)$ ($0<W(t)<W_{max}$) (see FIGS. 2 and 3).

Values of $HP(x)$ at preselected values of x, for example, $HP(10)$, $HP(50)$, and $HP(90)$ are computed as representative values of the lipophilic solvent ratio distribution, and the $HP(x)$ is regarded as an index of hydrophobicity. Most preferably, $HP(50)$ is computed as a representative value of the lipophilic solvent ratio distribution, and used as an index of hydrophobicity. Also, $HP(90)-HP(10)$ is computed as a measure for variation of the lipophilic solvent ratio distribution whereby the lipophilic solvent ratio can be evaluated.

In a preferred embodiment of the hydrophobicity analysis method, at least one solvent is selected from alcohols such as methanol, ethanol, isopropyl alcohol and butyl alcohol, and acetone as the lipophilic solvent, and water is selected as the hydrophilic solvent.

When the lipophilic solvent is methanol and the hydrophilic solvent is water, a powder having a parameter $HP(50)$ meeting $68.0 \leq HP(50)$ is evaluated as having a high degree of hydrophobicity.

When $HP(10)$ and $HP(90)$ are further computed in the water-methanol mixture, and $HP(90)-HP(10)$ is used as a measure for variation of the lipophilic solvent ratio, a powder meeting HP(90)-HP(10)≤22.0 is evaluated as having a small variation.

Alternatively, when the lipophilic solvent is ethanol and the hydrophilic solvent is water, a powder having a parameter HP(50) meeting 30.0≤HP(50) is evaluated as having a high degree of hydrophobicity.

When HP(10) and HP(90) are further computed in the water-ethanol mixture, a powder meeting HP(90)-HP(10) ≤28.0 is evaluated as having a small variation.

The degree of hydrophobicity of a pigment can be measured by the analysis method of the invention. As mentioned above, the solvent which is used as the lipophilic solvent is not particularly limited as long as it is miscible with water in any desired proportion. Among others, alcohols such as methanol, ethanol, isopropyl alcohol and butyl alcohol and acetone are preferred as the lipophilic solvent because of high solubility to water. Water is typically selected as the hydrophilic solvent.

[Pigment]

A further embodiment of the invention is a high-hydrophobicity-treated coloring pigment. A method for treating a pigment for obtaining the desired pigment is not particularly limited and any desired method may be used. The conditions of surface treatment may be optimized while monitoring the parameter HP(x) of hydrophobicity.

<Surface Treatment>

As used herein, the high-hydrophobicity-treated coloring pigment refers to a hydrophobic-treated pigment having a high degree of hydrophobicity, which is obtained from surface treatment of an inorganic or organic coloring pigment with a hydrophobic treating agent.

The hydrophobic treatment on the surface of a pigment is a technique commonly used to impart sufficient water repellency or satisfactory dispersibility. Particularly for coloring pigments to be blended in make-up cosmetics, hydrophobic treatment is effective for improving the water resistance and skin adhesion of pigments and for preventing make-up deterioration.

However, if a coloring pigment which has not been fully hydrophobized because of low accuracy of hydrophobic treatment is blended in a cosmetic composition, none of the above-mentioned effects are exerted, and rather a color separation phenomenon occurs due to sedimentation or separation as a result of the pigment agglomerating in the cosmetic composition. The cosmetic composition is thus exacerbated in stability with time, leading to a loss of aesthetic effect and a drop of commercial value. Such a phenomenon frequently develops with cosmetic compositions of emulsion type such as cream foundations and liquid foundations.

If the amount of a surfactant blended is increased in order to prevent the agglomeration and to improve the dispersion of a pigment, it gives rise to problems of feel-on-use such as a heavy and greasy feel-on-use.

The above-discussed problems can be overcome using the high-hydrophobicity-treated coloring pigment of the invention. There is obtained a cosmetic composition which has excellent aesthetic effect and stability with time, gives a pleasant feel on use, and is unsusceptible to make-up deterioration.

<Coloring Pigment>

The coloring pigment used herein is not particularly limited as long as it is commonly used for the purpose of coloring of cosmetics. Examples include red iron oxide, yellow iron oxide, white titanium oxide, black iron oxide, red iron oxide, ultramarine, Prussian blue, manganese violet, cobalt violet, chromium hydroxide, chromium oxide, cobalt oxide, cobalt titanate, iron oxide-doped titanium oxide, iron titanate, fired (titanium/titanium oxide), lithium cobalt titanate, cobalt titanate, titanium nitride, iron hydroxide, inorganic brown pigments such as γ-iron oxide, inorganic yellow pigments such as yellow ochre, and colored pigments such as tar-base dyes in lake form and natural dyes in lake form. Also inorganic colored pearl pigments include titanium oxide-coated mica, bismuth oxychloride, titanium oxide-coated bismuth oxychloride, titanium oxide-coated talc, fish scales, and titanium oxide-coated colored mica. Although any of the foregoing pigments can be used, preference is given to red iron oxide, yellow iron oxide, white titanium oxide, and black iron oxide.

The shape of the pigment used herein may be any of spherical, generally spherical, rod, spindle, petal, strip, and irregular shapes. The geometrical shape of the pigment is not particularly limited as long as cosmetic compositions can be colored therewith. In view of covering power, the pigment preferably has a particle size, specifically a volume average particle size of 150 to 600 nm. As used herein, the volume average particle size is an average of measurements at 10 points as observed under TEM. If the volume average particle size is less than 150 nm, the efficiency of coloration of a cosmetic composition may become low due to a lack of covering power. With a particle size in excess of 600 nm, the feel-on-use may be adversely affected.

Further, the pigment used herein may have been treated on the surface partially or entirely with an inorganic compound such as alumina, aluminum hydroxide, silica or hydrous silica.

<Hydrophobic Treating Agent>

The treating agent (hydrophobic treating agent) used for hydrophobic treatment of the coloring pigment according to the invention is not particularly limited as long as it can impart hydrophobicity. Suitable treating agents include organosilicon compounds, waxes, paraffins, organofluoro compounds such as perfluoroalkyl phosphates, surfactants, amino acids such as N-acylglutamic acid, and metal soaps such as aluminum stearate and magnesium myristate.

More preferred are organosilicon compounds. Examples include silanes or silylating agents such as caprylsilanes (AES-3083 by Shin-Etsu Chemical Co., Ltd.) and trimethoxysilyl dimethicone; silicone oils such as dimethylsilicones (KF-96A series by Shin-Etsu Chemical Co., Ltd.), methylhydrogen type polysiloxanes (KF-99P, KF-9901 by Shin-Etsu Chemical Co., Ltd.), silicone branched silicone treating agents (KF-9908, KF-9909 by Shin-Etsu Chemical Co., Ltd.); silicone compounds such as acrylic silicones (KP-574, KP-541 by Shin-Etsu Chemical Co., Ltd.). Inter alia, the powdered silicone treating agents described in JP 3912961 are preferably used. Especially, triethoxysilylethyl polydimethylsiloxyethylhexyl dimethicone (KF-9909 by Shin-Etsu Chemical Co., Ltd.) or dimethylpolysiloxane having triethoxysilyl, polydimethylsiloxyethyl and hexyl groups on side chains is preferred because it exhibits high affinity even when the dispersing medium in which the high-hydrophobicity-treated coloring pigment is dispersed is a silicone, hydrocarbon or a mixture thereof.

The hydrophobic treating agents may be used alone or in admixture.

<Surface Treatment Method>

In the practice of the invention, a method for treating a coloring pigment on its surface with a hydrophobic treating agent is not particularly limited. Surface treatment may be carried out by any well-known methods. The surface treatment method is generally divided into a dry method and a wet method. The dry method uses any suitable stirring, grinding, mixing and dispersing machines such as Henschel mixer, ball mill, jet mill, kneader, planetary mixer, sand mill, attritor, ribbon blender, disper mixer, and homomixer, whereby surface treatment is accomplished by mixing and contacting the coloring pigment with the hydrophobic treating agent. At this point, surface treatment may be carried out while applying energy such as heating, mechanical or mechanochemical power, or overheated steam. Alternatively, once the coloring pigment and the hydrophobic treating agent are fully mixed and contacted, energy may be separately applied to complete treatment such as by heating, mechanical or mechanochemical power, or overheated steam. Also in the step of mixing and contacting the coloring pigment with the hydrophobic treating agent, a means of previously dissolving or dispersing the hydrophobic treating agent in an arbitrary amount of water, solvent or supercritical fluid and spraying the resulting solution or dispersion to the coloring pigment may be employed for the purpose of improving the dispersion efficiency of the hydrophobic treating agent. The wet method involves the steps of dispersing the coloring pigment and the hydrophobic treating agent in water, solvent or supercritical fluid for mixing and contacting them, then evaporating the solvent, and separately applying energy such as heating, mechanical or mechanochemical power, or overheated steam.

In either method, preferably optimum conditions of the surface treatment are sought for using the hydrophobicity parameter $HP(x)$ as the index of evaluation.

Evaluating a variety of hydrophobic-treated coloring pigments by the above analysis method and making extensive investigations on the optimum treatment process for obtaining the pigment with a high accuracy of treatment, the inventors have found the surface-treated coloring pigment capable of exerting the outstandingly high hydrophobic function which is never accomplished in the prior art. Particularly when methanol is used as the lipophilic solvent and water is used as the hydrophilic solvent, a surface-treated coloring pigment having the following value of hydrophobicity parameter $HP(x)$ exerts a high hydrophobic function.

A coloring pigment meeting $68.0 \leq HP(50)$, preferably $68.0 \leq HP(50)$ and $HP(90)-HP(10) \leq 22.0$, particularly when the coloring pigment is a versatile red iron oxide pigment, yellow iron oxide pigment, white titanium oxide pigment or black iron oxide pigment, a red iron oxide pigment meeting $68.0 \leq HP(50)$, preferably additionally $HP(90)-HP(10) \leq 16.0$, a yellow iron oxide pigment meeting $68.0 \leq HP(50)$, preferably additionally $HP(90)-HP(10) \leq 22.0$, a white titanium oxide pigment meeting $73.0 \leq HP(50)$, preferably additionally $HP(90)-HP(10) \leq 20.0$, or a black iron oxide pigment meeting $72.5 \leq HP(50)$, preferably additionally $HP(90)-HP(10) \leq 9.0$;
preferably a red iron oxide pigment meeting $69.0 \leq HP(50)$, preferably additionally $HP(90)-HP(10) \leq 14.5$, a yellow iron oxide pigment meeting $69.0 \leq HP(50)$, preferably additionally $HP(90)-HP(10) \leq 20.5$, a white titanium oxide pigment meeting $73.5 \leq HP(50)$, preferably additionally $HP(90)-HP(10) \leq 18.5$, or a black iron oxide pigment meeting $73.5 \leq HP(50)$, preferably additionally $HP(90)-HP(10) \leq 8.4$;
more preferably a red iron oxide pigment meeting $70.0 \leq HP(50)$, preferably additionally $HP(90)-HP(10) \leq 13.0$, a yellow iron oxide pigment meeting $70.0 \leq HP(50)$, preferably additionally $HP(90)-HP(10) \leq 19.0$, a white titanium oxide pigment meeting $74.0 \leq HP(50)$, preferably additionally $HP(90)-HP(10) \leq 17.0$, or a black iron oxide pigment meeting $74.5 \leq HP(50)$, preferably additionally $HP(90)-HP(10) \leq 7.8$
is suited as the high-hydrophobicity-treated coloring pigment.

When ethanol is used as the lipophilic solvent and water is used as the hydrophilic solvent, a surface-treated coloring pigment having the following value of hydrophobicity parameter $HP(x)$ exerts a high hydrophobic function.

A coloring pigment meeting $30.0 \leq HP(50)$, preferably $30.0 \leq HP(50)$ and $HP(90)-HP(10) \leq 28.0$, particularly when the coloring pigment is a versatile red iron oxide pigment, yellow iron oxide pigment, white titanium oxide pigment or black iron oxide pigment, a red iron oxide pigment meeting $30.0 \leq HP(50)$, preferably additionally $HP(90)-HP(10) \leq 18.0$, a yellow iron oxide pigment meeting $30.0 \leq HP(50)$, preferably additionally $HP(90)-HP(10) \leq 21.0$, a white titanium oxide pigment meeting $36.0 \leq HP(50)$, preferably additionally $HP(90)-HP(10) \leq 19.0$, or a black iron oxide pigment meeting $40.0 \leq HP(50)$, preferably additionally $HP(90)-HP(10) \leq 18.0$;
preferably a red iron oxide pigment meeting $39.0 \leq HP(50)$, preferably additionally $HP(90)-HP(10) \leq 18.0$, a yellow iron oxide pigment meeting $39.0 \leq HP(50)$, preferably additionally $HP(90)-HP(10) \leq 21.0$, a white titanium oxide pigment meeting $43.0 \leq HP(50)$, preferably additionally $HP(90)-HP(10) \leq 19.0$, or a black iron oxide pigment meeting $41.0 \leq HP(50)$, preferably additionally $HP(90)-HP(10) \leq 18.0$,
is suited as the high-hydrophobicity-treated coloring pigment.

[Cosmetic Composition]

Embodiments for providing the cosmetic composition of the invention are described below in detail although the invention is not limited thereby.

The cosmetic composition of the invention is defined as comprising the high-hydrophobicity-treated coloring pigment defined above, while it may comprise other ingredients which are selected from well-known ingredients depending on the type of a particular cosmetic composition.

Although the amount of the high-hydrophobicity-treated coloring pigment blended herein may be selected as appropriate depending on the type of a particular cosmetic composition, the amount is typically 0.05 to 30.0% by weight, preferably 0.3 to 15.0% by weight of the overall cosmetic composition.

Since the inclusion of at least one of the surface-treated coloring pigments developing a high hydrophobicity function according to the invention is effective for preventing the pigment from agglomeration, sedimentation, and color separation, there is obtained a cosmetic composition having good aesthetic properties, stability over time, and a pleasant feel-on-use.

Various ingredients which are used in ordinary cosmetic compositions may be blended in the inventive cosmetic composition as long as the benefits of the invention are not compromised. Suitable ingredients include, for example, (1) oils, (2) compounds having alcoholic hydroxyl group, (3) surfactants, (4) other powders, (5) admixtures of crosslinked organopolysiloxane and normally liquid oil, (6) silicone waxes, (7) film-forming agents, and (8) other additives. These ingredients may be used alone or in any suitable combination of two or more.

(1) Oil

The oil may be either solid, semi-solid, or liquid. Examples include naturally occurring animal and plant oils and fats, semi-synthetic oils and fats, hydrocarbon oils, higher fatty acids, higher alcohols, ester oils, silicone oils, and fluorochemical oils.

Naturally occurring animal and plant oils and semi-synthetic oils

Suitable naturally occurring animal and plant oils and semi-synthetic oils include avocado oil, linseed oil, almond oil, insect wax, *perilla* oil, olive oil, cocoa butter, kapok wax, kaya oil, carnauba wax, liver oil, candelilla wax, purified candelilla wax, beef tallow, beef foot fat, beef bone fat, hardened beef tallow, persic oil, spermaceti, hardened oil, wheat germ oil, sesame oil, rice germ oil, rice bran oil, sugarcane wax, *camellia* oil, safflower oil, shea butter, Chinese tung oil, cinnamon oil, jojoba wax, squalane, squalene, shellac wax, turtle oil, soy oil, tea seed oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sun flower oil, grape oil, bayberry wax, jojoba oil, macadamia nut oil, bees wax, mink oil, meadowfoam oil, cotton seed oil, cotton wax, Japan wax, Japan kernel oil, montan wax, palm oil, hydrogenated palm oil, tri-coconut oil fatty acid glyceride, mutton, peanut oil, lanolin, liquid lanolin, reduced lanolin, lanolin alcohol, hard lanolin, lanolin acetate, lanolin alcohol acetate, isopropyl lanolin fatty acid, polyoxyethylene (POE) lanolin alcohol ether, POE lanolin alcohol acetate, lanolin fatty acid polyethylene glycol, POE hydrogenated lanolin alcohol ether, and egg yolk oil.

Hydrocarbon Oil

Suitable hydrocarbon oils include linear and branched hydrocarbon oils, which may be either volatile or nonvolatile. Examples include ozokerite, α-olefin oligomers, soft isoparaffin, isododecane, isohexadecane, soft liquid isoparaffin, squalane, synthetic squalane, vegetable squalane, squalene, ceresin, paraffin, paraffin wax, polyethylene wax, polyethylene-polypropylene wax, ethylene/propylene/styrene copolymers, butylene/propylene/styrene copolymers, liquid paraffin, liquid isoparaffin, pristane, polyisobutylene, hydrogenated polyisobutene, microcrystalline wax, and vaseline.

Higher Fatty Acid

Suitable higher fatty acids include lauric acid, myristic acid, palmitic acid, stearic acid, behenic acid, undecylenic acid, oleic acid, linoleic acid, linolenic acid, arachidic acid, eicosapentaenoic acid (EPA), docosahexaenoic acid (DHA), isostearic acid, and 12-hydroxystearic acid.

Higher Alcohol

Higher alcohols are, for example, alcohols preferably having at least 6 carbon atoms, more preferably 10 to 30 carbon atoms. Suitable higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecinol, cholesterol, phytosterol, POE cholesterol ether, monostearyl glycerol ether (batyl alcohol), and monooleyl glyceryl ether (selachyl alcohol).

Ester Oil

Examples of the ester oil include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyl dodecyl oleate, decyl oleate, neopentyl glycol dioctanoate, neopentyl glycol dicaprilate, triethyl citrate, 2-ethylhexyl succinate, pentyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyl dodecyl myristate, 2-hexyldecyl myristate, myristyl myristate, hexyl decyl dimethyloctanoate, ethyl laurate, hexyl laurate, N-lauroyl-L-glutamic acid 2-octyldodecyl ester, lauroyl sarcosine isopropyl ester, and diisostearyl malate; and glyceride oils such as acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

Silicone Oil

Examples of the silicone oil include linear or branched organopolysiloxanes ranging from low viscosity to high viscosity such as dimethylpolysiloxane, caprylylmethicone, phenyltrimethicone, methylphenylpolysiloxane, methylhexylpolysiloxane, methylhydrogenpolysiloxane, and dimethyl siloxane-methylphenylsiloxane copolymers; silicone rubbers such as amino-modified organopolysiloxane, pyrrolidone-modified organopolysiloxane, pyrrolidone carboxylic acid-modified organopolysiloxane, gum-like dimethylpolysiloxane having a high degree of polymerization, gum-like amino-modified organopolysiloxane, gum-like dimethyl siloxane-methylphenylsiloxane copolymers; and silicone gum, silicone gum in cyclic organopolysiloxane, trimethylsiloxysilicic acid, trimethylsiloxysilicic acid in cyclic siloxane, higher alkoxy-modified silicone (e.g., stearoxysilicone), higher fatty acid-modified silicone, alkyl-modified silicone, long chain alkyl-modified silicone, amino acid-modified silicone, fluorine-modified silicone, silicone resins, and solution forms of silicone resins.

Fluorochemical Oil

Suitable fluorochemical oils include perfluoropolyether, perfluorodecalin, and perfluorooctane.

(2) Alcoholic Hydroxyl Group-Containing Compound

Alcoholic hydroxyl group-containing compounds include lower alcohols of preferably 2 to 5 carbon atoms such as ethanol and isopropanol, and sucrose alcohols such as sorbitol and maltose. Also included are sterols such as cholesterol, citosterol, phytosterol, and lanosterol, and polyhydric alcohols such as butylene glycol, propylene glycol, dibutylene glycol, and pentylene glycol.

(3) Surfactant

Suitable surfactants include nonionic, anionic, cationic and ampholytic surfactants. Any of surfactants which are used in ordinary cosmetic compositions may be used without limitation. Among many surfactants, preference is given to partially crosslinked polyether-modified silicones, partially crosslinked polyglycerol-modified silicones, linear or branched polyoxyethylene-modified organopolysiloxanes, linear or branched polyoxyethylene polyoxypropylene-modified organopolysiloxanes, linear or branched polyoxyethylene/alkyl co-modified organopolysiloxanes, linear or branched polyoxyethylene polyoxypropylene/alkyl co-modified organopolysiloxanes, linear or branched polyglycerol-modified organopolysiloxanes, and linear or branched polyglycerol/alkyl co-modified organopolysiloxanes. In these surfactants, the content of a hydrophilic polyoxyethylene group, polyoxyethylene polyoxypropylene group or polyglycerol residue is preferably 10 to 70% by weight of the molecule. Exemplary surfactants include KSG-210, 240, 310, 320, 330, 340, 320Z, 350Z, 710, 810, 820, 830, 840, 820Z, 850Z, KF-6011, 6013, 6017, 6028, 6038, 6043, 6048, 6100, 6104, 6105, 6106 from Shin-Etsu Chemical Co., Ltd.

The amount of the surfactant blended is preferably 0.1 to 20% by weight of the overall cosmetic composition. Less than 0.1% by weight of the surfactant may sometimes fail to exert the dispersion or emulsification function. A cosmetic composition containing more than 20% by weight of the surfactant may present a greasy feel-on-use. The surfactant preferably has a HLB value of 2 to 14.5, but is not limited thereto.

(4) Other Powder

Besides the coloring pigment according to the invention, a powder ingredient may be blended in the cosmetic composition insofar as the benefits of the invention are not impaired. Suitable powders include inorganic powders, metal powders, organic powders, and inorganic/organic composite powders. Examples are described below.

Inorganic Powder

Suitable inorganic powders include microparticles of mica titanium, zirconium oxide, zinc oxide, cerium oxide, magnesium oxide, barium sulfate, calcium sulfate, magnesium sulfate, calcium carbonate, magnesium carbonate, talc, cleaved mica, mica, kaolin, sericite, muscovite, synthetic mica, phlogopite, trilithionite, biotite, lepidolite, silicic acid, silicon dioxide, fumed silica, hydrous silicon dioxide, aluminum silicate, magnesium silicate, aluminum magnesium silicate, calcium silicate, barium silicate, strontium silicate, tungstic acid metal salts, hydroxyapatite, vermiculite, gibbsite, bentonite, montmorillonite, hectorite, zeolite, ceramic powder, calcium secondary phosphate, alumina, aluminum hydroxide, boron nitride, and glass.

Metal Powder

Exemplary metal powders include microparticles of aluminum, copper, stainless steel and silver.

Organic Powder

Suitable organic powders include powders of silicone, polyamide, polyacrylic acid-acrylate, polyester, polyethylene, polypropylene, polystyrene, styrene-acrylic acid copolymers, divinylbenzene-styrene copolymers, polyurethane, vinyl resins, urea resins, melamine resins, benzoguanamine, polymethylbenzoguanamine, tetrafluoroethylene, polymethyl methacrylate, cellulose, silk, nylon, phenolic resins, epoxy resins, and polycarbonate. Specifically, silicone powders include silicone resin particles (e.g., KMP-590, KMP-591 by Shin-Etsu Chemical Co., Ltd.), and silicone resin-coated silicone rubber particles (e.g., KSP-100, 101, 102, 105, 300, 411, 441 by Shin-Etsu Chemical Co., Ltd.). Metal soaps are also included. Examples include powders of zinc stearate, aluminum stearate, calcium stearate, magnesium stearate, zinc myristate, magnesium myristate, zinc cetyl phosphate, calcium cetyl phosphate, and zinc sodium cetyl phosphate. Organic dyes are also included. Examples include synthetic dyes such as Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, and Orange #207; and natural dyes such as carminic acid, laccaic acid, carthamin, brazilin, and crocin.

Inorganic/Organic Composite Powder

Suitable inorganic/organic composite powders include composite powders in the form of inorganic particles (commonly used in cosmetics) which are surface covered with organic particles by any well-known standard technique.

The foregoing inorganic powders, metal powders, organic powders, and inorganic/organic composite powders may have been treated on particle surfaces with well-known surface treating agents, prior to use, insofar as the benefits of the invention are not significantly impaired.

(5) Admixture of Crosslinked Organopolysiloxane and Normally Liquid Oil

In conjunction with an admixture of a crosslinked organopolysiloxane and a normally liquid oil, it is preferred that the crosslinked organopolysiloxane polymer be swollen with the liquid oil by incorporating the liquid oil in an amount of more than its own weight. The liquid oil is typically selected from liquid silicone oils, hydrocarbon oils, ester oils, naturally occurring animal and plant oils, semi-synthetic oils, and fluorochemical oils in ingredient (1). Examples include silicone oils having a low viscosity of 0.65 $mm^2$/sec to 100.0 $mm^2$/sec at 25° C., hydrocarbon oils such as liquid paraffin, squalane, isododecane, and isohexadecane, glyceride oils such as trioctanoin, ester oils such as isotridecyl isononanoate, N-acylglutamic acid esters, and lauroyl sarcosine acid esters, and animal and plant oils such as macadamia nut oil. Ingredient (5) encompasses compounds of a partially crosslinked structure different from ingredient (3), which are free of polyether or polyglycerol structure in the molecular structure. Examples include KSG series (trade name) from Shin-Etsu Chemical Co., Ltd., specifically KSG-15, 1510, 16, 1610, 18A, 19, 41A, 42A, 43, 44, 042Z, 045Z, and 048Z.

(6) Silicone Wax

The silicone wax is preferably an acrylic silicone resin in the form of an acrylic/silicone graft or block copolymer. Also useful are acrylic silicone resins containing in the molecule at least one member selected from the group consisting of a pyrrolidone moiety, long-chain alkyl moiety, polyoxyalkylene moiety, fluoroalkyl moiety, and anionic moiety (e.g., carboxylic acid). Typical acrylic silicone graft copolymers are available under the trade name of KP-561P and 562P from Shin-Etsu Chemical Co., Ltd. Also preferably the silicone wax is a polylactone-modified polysiloxane, i.e., polysiloxane having attached thereto a polylactone which is a ring-opening polymerization product of a lactone compound having a five or more membered ring. Further the silicone wax may be a silicone-modified olefin wax obtained from addition reaction of an unsaturated group-containing olefin wax consisting of an α-olefin and a diene, with an organohydrogenpolysiloxane having at least one SiH bond in the molecule. In the olefin wax, preferred α-olefins are those of 2 to 12 carbon atoms such as ethylene, propylene, 1-butene, 1-hexene, and 4-methyl-1-pentene, and preferred diens include butadiene, isoprene, 1,4-hexadiene, vinyl norbornene, ethylidene norbornene, and dicyclopentadiene. The organohydrogenpolysiloxane having a SiH bond may be of a linear or siloxane branched structure.

(7) Film-Forming Agent

A film-forming agent may be added to the cosmetic composition mainly for the purpose of helping the cosmetic composition maintain its aesthetic effect. From the standpoint of imparting water repellency, the film-forming agent is preferably a silicone based composition though not limited thereto. Typical film-forming agents include trimethylsiloxysilicic acid, acrylic-silicone film former, silicone-modified norbornene, and silicone-modified pullulan. Specifically, the trimethylsiloxysilicic acid is available as KF-7312J, the acrylic-silicone film former as KP-545 and KP-549, the silicone-modified norbornene as NBN-30-ID, and the silicone-modified pullulan as TSPL-30-ID and TSPL-30-D5, all from Shin-Etsu Chemical Co., Ltd.

(8) Other Additives

Suitable other additives include oil-soluble gelling agents, antiperspirants, UV absorbers, UV absorbing/scattering agents, humectants, preservatives, bactericides, perfuming agents, salts, antioxidants, pH adjusting agents, chelating agents, refreshing agents, anti-inflammatory agents, skin improving agents (brightening agent, cell activating agent, anti-skin-roughening agent, blood flow promotor, skin astringent, antiseborrheic agent), vitamins, amino acids, nucleic acids, hormones, and inclusion compounds.

Oil-Soluble Gelling Agent

Suitable oil-soluble gelling agents include metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanoate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organo-modified clay minerals such as dimethylbenzyldodecylammonium montmorillonite clay, dimethyldioctadecylammonium montmorillonite clay, dimethyldioctadecylammonium hectorite clay.

Antiperspirant

Suitable antiperspirants include aluminum chlorohydrate, aluminum chloride, aluminum sesquichlorohydrate, zirconyl hydroxychloride, aluminum zirconium hydroxychloride, and aluminum zirconium glycine complex.

UV Absorber

Suitable UV absorbers include benzoic acid base UV absorbers such as p-aminobenzoic acid, anthranilic acid base UV absorbers such as methyl anthranilate, salicylic acid base UV absorbers such as methyl salicylate, octyl salicylate and trimethylcyclohexyl salicylate, cinnamic acid base UV absorbers such as octyl p-methoxycinnamate, benzophenone base UV absorbers such as 2,4-dihydroxybenzophenone, urocanic acid base UV absorbers such as ethyl urocanate, dibenzoylmethane base UV absorbers such as 4-t-butyl-4'-methoxy-dibenzoylmethane, phenyl benzimidazole sulfonic acid, and triazine derivatives.

UV Absorbing/Scattering Agent

Suitable UV absorbing/scattering agents include UV absorbing/scattering particles such as microparticulate titanium oxide, microparticulate iron-containing titanium oxide, microparticulate zinc oxide, microparticulate cerium oxide, and composites thereof. Dispersions of UV absorbing/scattering particles in oils are also acceptable. Examples of the dispersion of UV absorbing/scattering particles in oil include SPD series (trade name) from Shin-Etsu Chemical Co., Ltd., such as SPD-T5, Z5, T6, and Z6.

Humectant

Suitable humectants include glycerol, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate, polyoxyethylene methyl glucoside, polyoxypropylene methyl glucoside, egg yolk lecithin, soy lecithin, phosphatidylcholine, phosphatidyl ethanol amine, phosphatidyl serine, phosphatidyl glycerol, phosphatidyl inositol, and sphingophospholipid.

Preservative

Suitable preservatives include alkyl p-hydroxybenzoates, benzoic acid, sodium benzoate, sorbic acid, potassium sorbate, and phenoxyethanol. Suitable bactericides include benzoic acid, salicylic acid, carbolic acid, sorbic acid, alkyl p-hydroxybenzoates, p-chloro-m-cresol, hexachlorophene, benzalkonium chloride, chlorohexidine chloride, trichlorocarbaniride, photosensitizer, and phenoxyethanol.

Perfuming Agent

Perfuming agents include naturally occurring perfuming agents and synthetic perfuming agents. Suitable natural perfuming agents include plant perfuming agents extracted from flowers, leaves, trunks and skins, and animal perfuming agents such as musk and civet. Suitable synthetic perfuming agents include hydrocarbons such as monoterpene, alcohols such as aliphatic alcohols and aromatic alcohols, aldehydes such as terpene aldehydes and aromatic aldehydes, ketones such as alicyclic ketones, esters such as terpene base esters, lactones, phenols, oxides, nitrogen-containing compounds, and acetals.

Salt

Suitable salts include inorganic salts, organic acid salts, amine salts, and amino acid salts. Exemplary inorganic salts include sodium, potassium, magnesium, calcium, aluminum, zirconium and zinc salts of inorganic acids such as hydrochloric acid, sulfuric acid, carbonic acid, and nitric acid. Exemplary organic acid salts include salts of organic acids such as acetic acid, dehydroacetic acid, citric acid, malic acid, succinic acid, ascorbic acid, and stearic acid. Exemplary amine salts and amino acid salts include salts of amines such as triethanolamine, and salts of amino acids such as glutamic acid. In addition, hyaluronic acid, chondroitin sulfate and similar salts, aluminum zirconium glycine complex, and neutralized salts of acid-alkali as used in cosmetic formulation may be used.

Antioxidant

Suitable antioxidants include tocopherol, p-t-butylphenol, butyl hydroxyanisole, dibutylhydroxytoluene, and phytic acid.

pH Adjusting Agent

Suitable pH adjusting agents include lactic acid, citric acid, glycolic acid, succinic acid, tartaric acid, dl-malic acid, potassium carbonate, sodium hydrogencarbonate, and ammonium hydrogencarbonate.

Chelating Agent

Suitable chelating agents include alanine, sodium salt of EDTA, sodium polyphosphate, sodium metaphosphate, and phosphoric acid.

Refreshing Agent

Suitable refreshing agents include L-menthol and camphor.

Suitable anti-inflammatory agents include arantoin, glycyrrhizic acid and salts thereof, glycyrrhetinic acid, stearyl glycyrrhetinate, tranexamic acid and azulene.

Skin Improving Agent

Suitable skin improving agents include brightening agents such as placenta extract, arbutin, glutathione and Saxifrage stolonifera extract; cell activating agents such as royal jelly, photosensitizer, cholesterol derivatives, bovine blood extract; anti-skin-roughening agents; blood flow promotors such as nonanoic acid vanillylamide, benzyl nicotinate, β-butoxyethyl nicotinate, capsaicin, zingerone, cantharides tincture, ichthammol, caffeine, tannic acid, α-borneol, nicotinic acid tocopherol, inositol hexanicotinate, cyclandelate, cinnarizine, tolazoline, acetylcholine, verapamil, cepharanthine, and γ-oryzanol; skin astringents such as zinc oxide and tannic acid; antiseborrheic agents such as sulfur and thianthrol.

Vitamin

Suitable vitamins include vitamin A species such as vitamin A oil, retinol, retinol acetate, and retinol palmitate; vitamin B species, for example, vitamin B2 species such as riboflavin, riboflavin butyrate, and flavin adenine nucleotide, vitamin B6 species such as pyridoxine hydrochloride, pyridoxine dioctanoate, and pyridoxine tripalmitate, vitamin B12 and derivatives thereof, vitamin B15 and derivatives thereof; vitamin C species such as L-ascorbic acid, L-ascorbic acid dipalmitic acid ester, sodium L-ascorbic acid-2-sulfate, and dipotassium L-ascorbic acid phosphoric acid diester; vitamin D species such as ergocalciferol and cholecalciferol; vitamin E species such as α-tocopherol, β-tocopherol, γ-tocopherol, dl-α-tocopherol acetate, dl-α-tocopherol nicotinate, and dl-α-tocopherol succinate; nicotinic acids such as nicotinic acid, benzyl nicotinate and nicotinic acid amide; vitamin H; vitamin P; pantothenic acids such as calcium pantothenate, D-pantothenyl alcohol, pantothenyl ethyl ether, and acetylpantothenyl ethyl ether, and biotin.

Amino Acid

Suitable amino acids include glycine, valine, leucine, isoleucine, serine, threonine, phenylalanine, arginine, lysine, aspartic acid, glutamic acid, cystine, cysteine, methionine, and tryptophan.

Nucleic Acid

Typical of the nucleic acid is deoxyribonucleic acid.

Hormone

Suitable hormones include estradiol and ethenylestradiol.

Inclusion Compound

Typical of the inclusion compound is cyclodextrin.

The cosmetic composition may take the form of powder, oil and emulsion.

Suitable cosmetic compositions include those having the aforementioned cosmetic ingredients formulated therein, for example, skin care cosmetics such as lotion, milky lotion, cream, cleansing agent, pack, massage agent, beauty agent, beauty oil, cleansing cream, deodorant, hand cream, lip cream, wrinkle concealer; make-up cosmetics such as make-up primer, concealer, powder product, powder foundation, liquid foundation, cream foundation, oily foundation, cheek color, eye shadow, mascara, eye liner, eye brow, lipstick; nail care products such as enamel, undercoat, overcoat; hair care products such as shampoo, rinse, treatment, setting agent; antiperspirant products, and UV protection products such as sunscreen oil, sunscreen lotion and sunscreen cream.

The cosmetic composition exerts more outstanding effects when it is an emulsion composition. Exemplary emulsion compositions include water-in-oil emulsions, oil-in-water emulsions, non-aqueous emulsions, and multiple emulsions such as W/O/W and O/W/O emulsions.

EXAMPLES

Examples of the invention are given below by way of illustration. Notably, these examples are not intended to limit the scope of the invention thereto. KF-9909 by Shin-Etsu Chemical Co., Ltd. is used as triethoxysilylethyl polydimethylsiloxyethylhexyl dimethicone in Examples 1 to 18 and Reference Examples 1 to 4. As used herein, the volume average particle size is an average of measurements at 10 points as observed under TEM.

Sometimes, pigment is simply described as powder.

Example 1

(Preparation of Organic Solvent Dispersion of Silicone Oil)

A total 184 g of an organic solvent dispersion of silicone oil was obtained by mixing 24 g of triethoxysilylethyl polydimethylsiloxyethylhexyl dimethicone as silicone oil with 160 g of n-hexane.

(Preparation of Cosmetic Powder Surface-Treated with Triethoxysilylethyl Polydimethylsiloxyethylhexyl Dimethicone)

800 g of red iron oxide powder was admitted into a Henschel mixer. With stirring and mixing, 184 g of the organic solvent dispersion of silicone oil was sprayed to the powder. After the spraying, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 3% (external value) triethoxysilylethyl polydimethylsiloxyethylhexyl dimethicone. The powder had a volume average particle size of 200 nm.

Reference Example 1

(Silicone Oil)

24 g of triethoxysilylethyl polydimethylsiloxyethylhexyl dimethicone was used without dispersing in n-hexane.

(Preparation of Cosmetic Powder Surface-Treated with Triethoxysilylethyl Polydimethylsiloxyethylhexyl Dimethicone)

800 g of red iron oxide powder was admitted into a Henschel mixer. With stirring and mixing, 24 g of the silicone oil was sprayed to the powder. After the spraying, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 3% (external value) triethoxysilylethyl polydimethylsiloxyethylhexyl dimethicone. The powder had a volume average particle size of 200 nm.

Reference Example 2

(Preparation of Organic Solvent Dispersion of Silicone Oil)

A total 72 g of an organic solvent dispersion of silicone oil was obtained by mixing 24 g of triethoxysilylethyl polydimethylsiloxyethylhexyl dimethicone with 48 g of n-hexane.

(Preparation of Cosmetic Powder Surface-Treated with Triethoxysilylethyl Polydimethylsiloxyethylhexyl Dimethicone)

800 g of red iron oxide powder was admitted into a Henschel mixer. With stirring and mixing, 72 g of the organic solvent dispersion of silicone oil was added dropwise. After the dropwise addition, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 3% (external value) triethoxysilylethyl polydimethylsiloxyethylhexyl dimethicone. The powder had a volume average particle size of 200 nm.

Example 2

(Preparation of Organic Solvent Dispersion of Silicone Oil)

A total 65 g of an organic solvent dispersion of silicone oil was obtained by mixing 15 g of triethoxysilylethyl polydimethylsiloxyethylhexyl dimethicone with 50 g of n-hexane.

(Preparation of Cosmetic Powder Surface-Treated with Triethoxysilylethyl Polydimethylsiloxyethylhexyl Dimethicone)

500 g of yellow iron oxide powder was admitted into a Henschel mixer. With stirring and mixing, 65 g of the organic solvent dispersion of silicone oil was sprayed to the powder. Stirring and mixing was continued for achieving uniform surface treatment. During the stirring and mixing operation, the yellow iron oxide powder was scraped down within the Henschel mixer. The yellow iron oxide powder was taken out and allowed for reaction, obtaining the yellow iron oxide powder which was surface-treated with 3% (external value) triethoxysilylethyl polydimethylsiloxyethylhexyl dimethicone. The powder had a volume average particle size of 200 nm.

Reference Example 3

(Preparation of Organic Solvent Dispersion of Silicone Oil)

A total 15 g of an organic solvent dispersion of silicone oil was obtained by mixing 7.5 g of triethoxysilylethyl polydimethylsiloxyethylhexyl dimethicone with 7.5 g of n-hexane.

(Preparation of Cosmetic Powder Surface-Treated with Triethoxysilylethyl Polydimethylsiloxyethylhexyl Dimethicone)

750 g of red iron oxide powder was admitted into a Henschel mixer. With stirring and mixing, 15 g of the organic solvent dispersion of silicone oil was added dropwise. After the dropwise addition, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 1% (external value) triethoxysilylethyl polydimethylsiloxyethylhexyl dimethicone. The powder had a volume average particle size of 200 nm.

Reference Example 4

(Preparation of Organic Solvent Dispersion of Silicone Oil)

A total 30 g of an organic solvent dispersion of silicone oil was obtained by mixing 15 g of triethoxysilylethyl polydimethylsiloxyethylhexyl dimethicone with 15 g of n-hexane.

(Preparation of Cosmetic Powder Surface-Treated with Triethoxysilylethyl Polydimethylsiloxyethylhexyl Dimethicone)

750 g of red iron oxide powder was admitted into a Henschel mixer. With stirring and mixing, 30 g of the organic solvent dispersion of silicone oil was added dropwise. After the dropwise addition, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 2% (external value) triethoxysilylethyl polydimethylsiloxyethylhexyl dimethicone. The powder had a volume average particle size of 200 nm.

Example 3

(Preparation of Organic Solvent Dispersion of Silicone Oil)

A total 60 g of an organic solvent dispersion of silicone oil was obtained by mixing 30 g of triethoxysilylethyl polydimethylsiloxyethylhexyl dimethicone with 30 g of n-hexane.

(Preparation of Cosmetic Powder Surface-Treated with Triethoxysilylethyl Polydimethylsiloxyethylhexyl Dimethicone)

750 g of red iron oxide powder was admitted into a Henschel mixer. With stirring and mixing, 60 g of the organic solvent dispersion of silicone oil was added dropwise. After the dropwise addition, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 4% (external value) triethoxysilylethyl polydimethylsiloxyethylhexyl dimethicone. The powder had a volume average particle size of 200 nm.

Example 4

(Preparation of Organic Solvent Dispersion of Silicone Oil)

A total 224 g of an organic solvent dispersion of silicone oil was obtained by mixing 24 g of triethoxysilylethyl polydimethylsiloxyethylhexyl dimethicone with 200 g of n-hexane.

(Preparation of Cosmetic Powder Surface-Treated with Triethoxysilylethyl Polydimethylsiloxyethylhexyl Dimethicone)

800 g of red iron oxide powder was admitted into a Henschel mixer. With stirring and mixing, 224 g of the organic solvent dispersion of silicone oil was sprayed to the powder. After the spraying, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 3% (external value) triethoxysilylethyl polydimethylsiloxyethylhexyl dimethicone. The powder had a volume average particle size of 200 nm.

Example 5

(Preparation of Organic Solvent Dispersion of Silicone Oil)

A total 60 g of an organic solvent dispersion of silicone oil was obtained by mixing 30 g of triethoxysilylethyl polydimethylsiloxyethylhexyl dimethicone with 30 g of n-hexane.

(Preparation of Cosmetic Powder Surface-Treated with Triethoxysilylethyl Polydimethylsiloxyethylhexyl Dimethicone)

1500 g of black iron oxide powder was admitted into a Henschel mixer. With stirring and mixing, 60 g of the organic solvent dispersion of silicone oil was sprayed to the powder. Stirring and mixing was continued for achieving uniform surface treatment. During the stirring and mixing operation, the black iron oxide powder was scraped down within the Henschel mixer. The black iron oxide powder was taken out and allowed for reaction, obtaining the black iron oxide powder which was surface-treated with 2.0% (external value) triethoxysilylethyl polydimethylsiloxyethylhexyl dimethicone. The powder had a volume average particle size of 300 nm.

Example 6

(Preparation of Organic Solvent Dispersion of Silicone Oil)

A total 75 g of an organic solvent dispersion of silicone oil was obtained by mixing 37.5 g of triethoxysilylethyl polydimethylsiloxyethylhexyl dimethicone with 37.5 g of n-hexane.

(Preparation of Cosmetic Powder Surface-Treated with Triethoxysilylethyl Polydimethylsiloxyethylhexyl Dimethicone)

1500 g of white titanium oxide powder was admitted into a Henschel mixer and premixed therein. With stirring and mixing, 75 g of the organic solvent dispersion of silicone oil was sprayed to the powder. After the spraying, stirring and mixing was continued for achieving uniform surface treatment. During the stirring and mixing operation, the white titanium oxide powder was scraped down within the Henschel mixer. The white titanium oxide powder was taken out and allowed for reaction, obtaining the white titanium oxide powder which was surface-treated with 2.5% (external value) triethoxysilylethyl polydimethylsiloxyethylhexyl dimethicone. The powder had a volume average particle size of 250 nm.

Example 7

(Preparation of Organic Solvent Dispersion of Silicone Oil)

A total 720 g of an organic solvent dispersion of silicone oil was obtained by mixing 360 g of triethoxysilylethyl polydimethylsiloxyethylhexyl dimethicone with 360 g of n-hexane.

(Preparation of Cosmetic Powder Surface-Treated with Triethoxysilylethyl Polydimethylsiloxyethylhexyl Dimethicone)

12 kg of red iron oxide powder was admitted into a Henschel mixer and premixed therein. With stirring and mixing, 720 g of the organic solvent dispersion of silicone oil was sprayed to the powder. After the spraying, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 3% (external value) triethoxysilylethyl polydimethylsiloxyethylhexyl dimethicone.

(Disintegration of Cosmetic Powder on Pin Mill)

The red iron oxide powder which was surface-treated with 3% triethoxysilylethyl polydimethylsiloxyethylhexyl dimethicone was admitted into a pin mill where the powder was disintegrated. The powder had a volume average particle size of 200 nm.

Example 8

(Preparation of Organic Solvent Dispersion of Silicone Oil)

A total 600 g of an organic solvent dispersion of silicone oil was obtained by mixing 300 g of triethoxysilylethyl polydimethylsiloxyethylhexyl dimethicone with 300 g of n-hexane.

(Preparation of Cosmetic Powder Surface-Treated with Triethoxysilylethyl Polydimethylsiloxyethylhexyl Dimethicone)

10 kg of yellow iron oxide powder was admitted into a Henschel mixer and premixed therein. With stirring and mixing, 600 g of the organic solvent dispersion of silicone oil was sprayed to the powder. Stirring and mixing was continued for achieving uniform surface treatment. During the stirring and mixing operation, the yellow iron oxide powder was scraped down within the Henschel mixer. The yellow iron oxide powder was taken out and allowed for reaction, obtaining the yellow iron oxide powder which was surface-treated with 3% (external value) triethoxysilylethyl polydimethylsiloxyethylhexyl dimethicone.

(Disintegration of Cosmetic Powder on Pin Mill)

The yellow iron oxide powder which was surface-treated with 3% triethoxysilylethyl polydimethylsiloxyethylhexyl dimethicone was admitted into a pin mill where the powder was disintegrated. The powder had a volume average particle size of 200 nm.

Example 9

(Preparation of Organic Solvent Dispersion of Silicone Oil)

A total 600 g of an organic solvent dispersion of silicone oil was obtained by mixing 300 g of triethoxysilylethyl polydimethylsiloxyethylhexyl dimethicone with 300 g of n-hexane.

(Preparation of Cosmetic Powder Surface-Treated with Triethoxysilylethyl Polydimethylsiloxyethylhexyl Dimethicone)

15 kg of black iron oxide powder was admitted into a Henschel mixer and premixed therein. With stirring and mixing, 600 g of the organic solvent dispersion of silicone oil was sprayed to the powder. After the spraying, stirring and mixing was continued for achieving uniform surface treatment. During the stirring and mixing operation, the black iron oxide powder was scraped down within the Henschel mixer. The black iron oxide powder was taken out and allowed for reaction, obtaining the black iron oxide powder which was surface-treated with 2% (external value) triethoxysilylethyl polydimethylsiloxyethylhexyl dimethicone.

(Disintegration of Cosmetic Powder on Pin Mill)

The black iron oxide powder which was surface-treated with 2% (external value) triethoxysilylethyl polydimethylsiloxyethylhexyl dimethicone was admitted into a pin mill where the powder was disintegrated. The powder had a volume average particle size of 300 nm.

Example 10

(Preparation of Organic Solvent Dispersion of Silicone Oil)

A total 750 g of an organic solvent dispersion of silicone oil was obtained by mixing 375 g of triethoxysilylethyl polydimethylsiloxyethylhexyl dimethicone with 375 g of n-hexane.

(Preparation of Cosmetic Powder Surface-Treated with Triethoxysilylethyl Polydimethylsiloxyethylhexyl Dimethicone)

15 kg of white titanium oxide powder was admitted into a Henschel mixer and premixed therein. With stirring and mixing, 750 g of the organic solvent dispersion of silicone oil was sprayed to the powder. After the spraying, stirring and mixing was continued for achieving uniform surface treatment. During the stirring and mixing operation, the titanium oxide powder was scraped down within the Henschel mixer. The titanium oxide powder was taken out and allowed for reaction, obtaining the white titanium oxide powder which was surface-treated with 2.5% (external value) triethoxysilylethyl polydimethylsiloxyethylhexyl dimethicone.

(Disintegration of Cosmetic Powder on Pin Mill)

The white titanium oxide powder which was surface-treated with 2.5% (external value) triethoxysilylethyl polydimethylsiloxyethylhexyl dimethicone was admitted into a pin mill where the powder was disintegrated. The powder had a volume average particle size of 250 nm.

[Test 1]

The surface-treated iron oxide powders obtained in Examples 1 and 2 and Reference Examples 1 and 2 were evaluated for dispersion and analyzed by the prior art hydrophobicity measurement method.

The evaluation of dispersion and the prior art hydrophobicity measurement method are as follows.

(Evaluation of Dispersion)

A 20-mL vial was charged with 10 g of cyclopentasiloxane, after which 0.05 g of the triethoxysilylethyl polydimethylsiloxyethylhexyl dimethicone-treated powder was added. The contents were mixed by operating a homogenizer (Ultrasonic Homogenizer US-150E) at the maximum level for 1 minute, obtaining a dispersion. After 10 g of purified water was added to the dispersion, the vial was shaken 20 times and allowed to stand. Evaluation was made by visually inspecting the dispersion of the surface-treated pigment in the silicone. When the surface-treated state is good, the pigment is fully dispersed in the silicone, defining a definite interface with water. Inversely when the surface-treated pigment state is poor, i.e., when the pigment fails to develop full repellency to water, the surface-treated pigment is wetted with water, and the interface between two liquids becomes vague.

Judgment is made according to the following criteria.

○: powder separated, interface at high position and without distortion

Δ: powder separated, but interface at low position and distorted

X: powder not separated

The results are shown in FIG. 4.

(Prior Art Hydrophobicity Measurement Method)

0.2 g of the triethoxysilylethyl polydimethylsiloxyethylhexyl dimethicone-treated powder was weighed into a 300-mL beaker and 50 ml of purified water was added. With electromagnetic stirring, methanol was added below the water surface. The time when the treated powder was wetted was the start point, and the time when the treated powder was no longer recognized on the water surface was the end point. From the volume of methanol required, the degree of hydrophobicity at the start point or the end point was computed according to the following equation. The results are shown in Table 1.

Degree of hydrophobicity (methanol concentration) $(\%) = [x/(50+x)] \times 100$ wherein x is the volume (mL) of methanol used.

TABLE 1

|  | Example 1 (N = 5) | | | | Reference Example 1 (N = 5) | | | |
| --- | --- | --- | --- | --- | --- | --- | --- | --- |
|  | Start point (mL) | Hydrophobicity at start point (%) | End point (mL) | Hydrophobicity at end point (%) | Start point (mL) | Hydrophobicity at start point (%) | End point (mL) | Hydrophobicity at end point (%) |
| Average | 139.0 | 73.5 | 202.6 | 80.2 | 66.2 | 57.0 | 147.2 | 74.6 |
| Standard deviation | 5.5 | 0.8 | 2.7 | 0.2 | 1.3 | 0.5 | 1.3 | 0.2 |
| Standard error | 2.4 | 0.4 | 1.2 | 0.1 | 0.6 | 0.2 | 0.6 | 0.1 |

|  | Reference Example 2 (N = 5) | | | | Example 2 (N = 5) | | | |
| --- | --- | --- | --- | --- | --- | --- | --- | --- |
|  | Start point (mL) | Hydrophobicity at start point (%) | End point (mL) | Hydrophobicity at end point (%) | Start point (mL) | Hydrophobicity at start point (%) | End point (mL) | Hydrophobicity at end point (%) |
| Average | 90.4 | 64.4 | 186.2 | 78.8 | 131.0 | 72.4 | 201.8 | 80.1 |
| Standard deviation | 1.5 | 0.4 | 3.8 | 0.3 | 2.2 | 0.3 | 2.9 | 0.2 |
| Standard error | 0.7 | 0.2 | 1.7 | 0.2 | 1.0 | 0.2 | 1.3 | 0.1 |

[Test 2]

Measurement errors due to an observer during the measurement of the surface-treated iron oxide powder obtained in Example 1 by the prior art hydrophobicity measurement method in Test 1 were confirmed. The results are shown in Table 2.

TABLE 2

|  | Observer A (N = 3) | | | Observer B (N = 3) | | | Observer C (N = 3) | |
| --- | --- | --- | --- | --- | --- | --- | --- | --- |
|  | Hydrophobicity at start point (%) | Hydrophobicity at end point (%) |  | Hydrophobicity at start point (%) | Hydrophobicity at end point (%) |  | Hydrophobicity at start point (%) | Hydrophobicity at end point (%) |
| Average | 62.1 | 75.6 | Average | 54.4 | 72.6 | Average | 55.8 | 72.9 |
| Standard deviation | 2.5 | 2.4 | Standard deviation | 6.2 | 1.1 | Standard deviation | 4.1 | 0.6 |
| Standard error | 1.4 | 1.4 | Standard error | 3.6 | 0.6 | Standard error | 2.4 | 0.4 |

As seen from Tables 1 and 2 and FIG. 4, when the accurate judgment of quality (good or bad) is difficult with the evaluation of dispersion because of qualitative evaluation, the prior art hydrophobicity measurement method in Test 1, which relies on visual judgment, has the problems that the standard error tends to increase and measurements significantly differ among observers.

[Test 3]

For the surface-treated iron oxide powder obtained in Example 2, the analysis results by the prior art hydrophobicity analysis method using a wettability tester of Rhesca Co., Ltd. are compared with the analysis results according to the invention. The results are shown in Table 3.

The prior art hydrophobicity analysis method and the inventive hydrophobicity analysis method are as follows.

(Prior Art Hydrophobicity Analysis Method)

A wettability tester WET-1001 of Rhesca Co., Ltd. was used. Relative to a lipophilic solvent volume ratio (%) corresponding to the lowest voltage rate, a voltage rate (%), and a slope, a lipophilic solvent volume ratio (%) and a voltage rate (%) crossing a straight line of voltage rate 100% are defined as the point when the powder starts wetting, from which a hydrophobicity degree was computed. The results are shown in Table 3.

$$\text{Hydrophobicity degree } (\%) = \{100 - y_0/a\} \times x_0$$

wherein $x_0$ is a lipophilic solvent volume ratio (%) corresponding to the lowest slope, $y_0$ is a voltage rate (%) corresponding to the lowest slope, and "a" is the lowest slope.

(Inventive Hydrophobicity Analysis Method)

By using a wettability tester WET-1001 of Rhesca Co., Ltd. and combining methanol as lipophilic solvent and water as hydrophilic solvent, 300 mL of a solvent mixture containing 60 or 65% by volume of methanol was prepared. To the solvent mixture was added 0.04 g of the triethoxysilylethyl polydimethylsiloxyethylhexyl dimethicone surface-treated red iron oxide powder in Example 2. While methanol was continuously added at a rate of 10 mL/min under stirring at a speed 500 rpm, a voltage rate correlating to a powder dispersion concentration in the solvent mixture was measured at intervals of 0.016-0.017 second, relative to the methanol volume ratio. For data discrete values as measured, the voltage rate observed relative to time series $t_i$ (wherein i is an integer, $t_i < t_{i+1}$) is $R_i$, and a lipophilic solvent volume ratio corresponding thereto is $HP_i$. For the voltage rate R, an average of total 11 measurement data including a certain voltage rate and forward and aft 5 points was determined for averaging to reduce the influence of noise.

[Math. 20]

$$\overline{R_i} = \sum_{i=-5}^{5} R_i$$

Provided that the maximum of voltage rate is 100 and the minimum of averaged voltage rate is $$\overline{R_{min}},$$ [Math. 21]

a parameter correlating to a powder dispersion concentration relative to an arbitrary voltage rate R in the range:

$$\overline{R_{min}} \leq R < 100$$ [Math. 22]

is defined as

[Math. 23]

$$x = \frac{100 - R}{100 - \overline{R_{min}}} \times 100 \quad (\text{wherein } 0 < x < 100)$$

and a lipophilic solvent ratio corresponding to x is represented by HP(x), for R meeting the range:

$$\overline{R_{i+1}} \leq R < \overline{R_i}$$ [Math. 24]

a continuous function of lipophilic solvent ratio is defined by HP(x):

[Math. 25]

$$HP(x) = \frac{HP_{i+1} - HP_i}{\overline{R_{i+1}} - \overline{R_i}} \times (R - \overline{R_i}) + HP_i$$

(see FIG. 1). Then a distribution function of lipophilic solvent ratio was obtained with respect to a parameter x (0<x<100) which changes in proportion to a powder dispersion concentration c(t) (0<c(t)<$c_{max}$) or cumulative sedimentation weight W(t) (0<W(t)<$W_{max}$) (see FIGS. 2 and 3).

HP(10), HP(50), and HP(90) were computed as representative values of the lipophilic solvent ratio distribution. Also, HP(90)-HP(10) was computed as an index for variation of the lipophilic solvent ratio distribution. The results are shown in Table 3.

TABLE 3

| Results of prior art hydrophobicity analysis (Example 2) | | | | | |
|---|---|---|---|---|---|
| | $y_0$ | $x_0$ | a | y | N = 5 Hydrophobicity |
| Average | 66.6 | 74.7 | −23.5 | 100.0 | 73.2 |
| Standard deviation | 3.8 | 1.3 | 5.1 | 0.0 | 1.2 |
| Standard error | 1.7 | 0.6 | 2.3 | 0.0 | 0.5 |

| Results of inventive hydrophobicity analysis (Example 2) | | |
|---|---|---|
| | | N = 5 |
| | HP(10) (%) | HP(50) (%) | HP(90) (%) |
| Average | 70.7 | 73.5 | 76.0 |
| Standard deviation | 0.6 | 0.4 | 0.8 |
| Standard error | 0.3 | 0.2 | 0.3 |

As is evident from Table 3, the standard error is very small in the inventive hydrophobicity analysis method as compared with the prior art hydrophobicity analysis method.

[Test 4]

On the surface-treated iron oxide powders obtained in Reference Examples 3, 4 and Example 3, the evaluation of dispersion in Test 1 and the inventive hydrophobicity analysis were carried out. The results are shown in FIG. 5 and Table 4.

In this test, hydrophobicity was measured by the same procedure as in Test 3 aside from using a water/methanol solvent mixture containing 60% by volume of methanol and 0.04 g of the powder in each of Reference Examples 3, 4 and Example 3.

TABLE 4

|  | Reference Example 3 | Reference Example 4 | Example 3 |
|---|---|---|---|
| Evaluation of dispersion | X | Δ | ○ |
| HP(10) (%) | 37.7 | 63.6 | 67.4 |
| HP(50) (%) | 41.7 | 65.7 | 72.7 |
| HP(90) (%) | 46.9 | 71.0 | 78.0 |
| HP(90) − HP(10) (%) | 9.2 | 7.4 | 10.6 |
| HP(100) (%) | 51.1 | 73.4 | 80.7 |
| Voltage MIN (%) | 39.4 | 52.8 | 69.9 |

As is evident from Table 4 and FIG. 5, the treated powder showing inferior evaluation results of dispersion like Reference Example 3 also showed inferior results of the inventive hydrophobicity measurement using a wettability tester. Reference Example 4 and Example 3 showing better evaluation results of dispersion than Reference Example 3 also showed superior results of the inventive hydrophobicity measurement to Reference Example 3. It is thus demonstrated that the evaluation of dispersion is in general agreement with the results of the inventive hydrophobicity measurement. However, a comparison between Reference Example 4 and Example 3 reveals that the accurate judgment of good or bad from the evaluation results of dispersion is difficult although Example 3 seems slightly better than Reference Example 4, whereas the results of the inventive hydrophobicity measurement are different. This indicates that since the evaluation of dispersion is a visual evaluation, equivalent results can lead to an error of evaluation. It is thus recommended to use the inventive hydrophobicity measurement method having a high accuracy of measurement and giving quantitative backings for actual sensory evaluation.

[Test 5]

On the surface-treated iron oxide powders and the surface-treated titanium oxide powders obtained in Examples 1, 4 to 6 and Reference Examples 1 and 2, the evaluation of dispersion in Test 1 and the inventive hydrophobicity analysis were carried out. The results are shown in Table 5 and FIG. 6.

In this test, hydrophobicity was measured by the same procedure as in Test 3 aside from using a water/methanol solvent mixture containing 60% by volume of methanol in Examples 1, 4, 6 and Reference Examples 1, 2, a water/methanol solvent mixture containing 65% by volume of methanol in Example 5 and 0.04 g of the powder in each Example.

TABLE 5

|  | Example 1 | Reference Example 1 | Reference Example 2 | Example 4 | Example 5 | Example 6 |
|---|---|---|---|---|---|---|
| Evaluation of dispersion | ○ | Δ | Δ | ○ | ○ | ○ |
| HP(10) (%) | 72.7 | 62.3 | 62.6 | 72.1 | 73.4 | 70.5 |
| HP(50) (%) | 74.0 | 64.7 | 66.0 | 74.7 | 75.8 | 74.4 |
| HP(90) (%) | 75.5 | 68.5 | 69.6 | 76.7 | 80.1 | 76.0 |
| HP(90) − HP(10) (%) | 2.7 | 6.2 | 7.0 | 4.6 | 6.7 | 5.5 |
| HP(100) (%) | 78.6 | 73.7 | 71.7 | 78.2 | 82.7 | 78.6 |
| Voltage MIN (%) | 66.3 | 54.3 | 49.1 | 56.4 | 67.2 | 84.2 |

As is evident from Table 5 and FIG. 6, the evaluation of dispersion gives vague differences because of visual judgment whereas the quantitative analysis using a lipophilic solvent ratio enables more detailed analysis, making it possible to judge the extent and uniformity of treatment of the treated powder.

[Test 6]

On the surface-treated iron oxide and titanium oxide powders obtained in Examples 7 to 10, as disintegrated, the inventive hydrophobicity analysis was carried out. The results are shown in Table 6.

In this test, hydrophobicity was measured by the same procedure as in Test 3 aside from using a water/methanol solvent mixture containing 60% by volume of methanol in Examples 7, 8, and 10, a water/methanol solvent mixture containing 65% by volume of methanol in Example 9, and 0.04 g of the powder in each Example.

TABLE 6

|  | HP(10) (%) | HP(50) (%) | HP(90) (%) | HP(90) − HP(10) (%) | HP(100) (%) |
|---|---|---|---|---|---|
| Example 7 | 67.9 | 74.2 | 77.8 | 9.9 | 80.7 |
| Example 8 | 63.7 | 73.6 | 79.3 | 15.6 | 80.7 |
| Example 9 | 71.4 | 76.4 | 79.0 | 7.6 | 83.2 |
| Example 10 | 64.5 | 73.2 | 78.9 | 14.4 | 80.7 |

As is evident from Table 6, the powders have excellent hydrophobicity even after disintegration.

Of the results of the inventive hydrophobicity analysis on the surface-treated iron oxide and titanium oxide powders obtained in Examples 1, 2, 5 to 10, the values of HP(50) and HP(90)-HP(10) for each powder color are summarized in Table 7.

TABLE 7

|  | HP(10) (%) | HP(50) (%) | HP(90) (%) | HP(90) − HP(10) (%) | HP(100) (%) |
|---|---|---|---|---|---|
| Red powder |  |  |  |  |  |
| Example 1 | 72.7 | 74.0 | 75.5 | 2.7 | 78.6 |
| Example 7 | 67.9 | 74.2 | 77.8 | 9.9 | 80.7 |
| Yellow powder |  |  |  |  |  |
| Example 2 | 70.7 | 73.5 | 76.0 | 5.3 | 79.5 |
| Example 8 | 63.7 | 73.6 | 79.3 | 15.6 | 80.7 |
| White powder |  |  |  |  |  |
| Example 6 | 70.5 | 74.4 | 76.0 | 5.5 | 78.6 |
| Example 10 | 64.5 | 73.2 | 78.9 | 14.4 | 80.7 |
| Black powder |  |  |  |  |  |
| Example 5 | 73.4 | 75.8 | 80.1 | 6.7 | 82.7 |
| Example 9 | 71.4 | 76.4 | 79.0 | 7.6 | 83.0 |

It is understood from the results in Table 7 that red iron oxide pigments wherein 68.0≤HP(50) and HP(90)-HP(10)≤16.0, yellow iron oxide pigments wherein 68.0≤HP(50) and HP(90)-HP(10)≤22.0, white titanium oxide pigments wherein 73.0≤HP(50) and HP(90)-HP(10)≤20.0, and black iron oxide pigments wherein 72.5≤HP(50) and HP(90)-HP(10)≤9.0, develop a high hydrophobicity when the lipophilic solvent is methanol.

Furthermore, surface-treated iron oxide powders and surface-treated titanium oxide powders were obtained by the surface treatment procedures described in Examples 11 to 14.

Example 11

(Preparation of Organic Solvent Dispersion of Silicone Oil)

A total 45 g of an organic solvent dispersion of silicone oil was obtained by mixing 22.5 g of triethoxysilylethyl polydimethylsiloxyethylhexyl dimethicone with 22.5 g of n-hexane.

(Preparation of Cosmetic Powder Surface-Treated with Triethoxysilylethyl Polydimethylsiloxyethylhexyl Dimethicone)

750 g of red iron oxide powder was admitted into a Henschel mixer. With stirring and mixing, 45 g of the organic solvent dispersion of silicone oil was sprayed to the powder. After the spraying, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 3% (external value) triethoxysilylethyl polydimethylsiloxyethylhexyl dimethicone.

Example 12

(Preparation of Organic Solvent Dispersion of Silicone Oil)

A total 90 g of an organic solvent dispersion of silicone oil was obtained by mixing 45.0 g of triethoxysilylethyl polydimethylsiloxyethylhexyl dimethicone with 45.0 g of n-hexane.

(Preparation of Cosmetic Powder Surface-Treated with Triethoxysilylethyl Polydimethylsiloxyethylhexyl Dimethicone)

1500 g of white titanium oxide powder was admitted into a Henschel mixer. With stirring and mixing, 90 g of the organic solvent dispersion of silicone oil was sprayed to the powder. After the spraying, stirring and mixing was continued for achieving uniform surface treatment. During the stirring and mixing operation, the white titanium oxide powder was scraped down within the Henschel mixer. The white titanium oxide powder was taken out and allowed for reaction, obtaining the white titanium oxide powder which was surface-treated with 3% (external value) triethoxysilylethyl polydimethylsiloxyethylhexyl dimethicone.

Example 13

(Preparation of Organic Solvent Dispersion of Silicone Oil)

A total 45 g of an organic solvent dispersion of silicone oil was obtained by mixing 22.5 g of triethoxysilylethyl polydimethylsiloxyethylhexyl dimethicone with 22.5 g of n-hexane.

(Preparation of Cosmetic Powder Surface-Treated with Triethoxysilylethyl Polydimethylsiloxyethylhexyl Dimethicone)

750 g of yellow iron oxide powder was admitted into a Henschel mixer. With stirring and mixing, 45 g of the organic solvent dispersion of silicone oil was sprayed to the powder. After the spraying, stirring and mixing was continued for achieving uniform surface treatment. During the stirring and mixing operation, the yellow iron oxide powder was scraped down within the Henschel mixer. The yellow iron oxide powder was taken out and allowed for reaction, obtaining the yellow iron oxide powder which was surface-treated with 3% (external value) triethoxysilyl ethyl polydimethylsiloxyethylhexyl dimethicone.

Example 14

(Preparation of Organic Solvent Dispersion of Silicone Oil)

A total 600 g of an organic solvent dispersion of silicone oil was obtained by mixing 300 g of triethoxysilylethyl polydimethylsiloxyethylhexyl dimethicone with 300 g of n-hexane.

(Preparation of Cosmetic Powder Surface-Treated with Triethoxysilylethyl Polydimethylsiloxyethylhexyl Dimethicone)

15 kg of black iron oxide powder was admitted into a Henschel mixer. With stirring and mixing, 600 g of the organic solvent dispersion of silicone oil was sprayed to the powder. After the spraying, stirring and mixing was continued for achieving uniform surface treatment. During the stirring and mixing operation, the black iron oxide powder was scraped down within the Henschel mixer. The black iron oxide powder was taken out and allowed for reaction, obtaining the black iron oxide powder which was surface-treated with 2% (external value) triethoxysilylethyl polydimethylsiloxyethylhexyl dimethicone.

(Disintegration of Cosmetic Powder by Hammer Mill)

The black iron oxide powder which was surface-treated with 2% (external value) triethoxysilylethyl polydimethylsiloxyethylhexyl dimethicone was admitted into a hammer mill where the powder was disintegrated.

On the surface-treated pigments obtained in Examples 11 to 14, the inventive hydrophobicity analysis was carried out using methanol as the lipophilic solvent. Parameters HP(50) and HP(90)-HP(10) are shown in Table 8.

In this test, hydrophobicity was measured by the same procedure as in Test 3 aside from using a solvent mixture containing 60% by volume of methanol in Runs 1, 2, and 3 in Table 8, a solvent mixture containing 65% by volume of methanol in Run 4 in Table 8, and 0.04 g of the powder in each run.

TABLE 8

| | | Hydrophobicity | |
|---|---|---|---|
| | Ingredients | HP(50) | HP(90) – HP(10) |
| 1 | triethoxysilylethyl polydimethylsiloxyethylhexyl dimethicone surface-treated white titanium oxide powder (Example 12) | 77.1 | 3.2 |
| 2 | triethoxysilylethyl polydimethylsiloxyethylhexyl dimethicone surface-treated yellow iron oxide powder (Example 13) | 73.2 | 10.4 |

TABLE 8-continued

| | Ingredients | Hydrophobicity | |
|---|---|---|---|
| | | HP(50) | HP(90) − HP(10) |
| 3 | triethoxysilylethyl polydimethylsiloxyethylhexyl dimethicone surface-treated red iron oxide powder (Example 11) | 72.1 | 4.2 |
| 4 | triethoxysilylethyl polydimethylsiloxyethylhexyl dimethicone surface-treated black iron oxide powder (Example 14) | 76.0 | 6.4 |

The surface-treated pigments of Examples 11 to 14 within the scope of the invention are high-hydrophobicity-treated coloring pigments meeting the following parameters:
red iron oxide pigments wherein 70.0≤HP(50) and HP(90)-HP(10)≤13.0,
yellow iron oxide pigments wherein 70.0≤HP(50) and HP(90)-HP(10)≤19.0,
white titanium oxide pigments wherein 74.0≤HP(50) and HP(90)-HP(10)≤17.0, and
black iron oxide pigments wherein 74.5≤HP(50) and HP(90)-HP(10)≤7.8.

Example 15

(Preparation of Organic Solvent Dispersion of Silicone Oil)
A total 720 g of an organic solvent dispersion of silicone oil was obtained by mixing 360 g of triethoxysilylethyl polydimethylsiloxyethylhexyl dimethicone as silicone oil with 360 g of n-hexane.
(Preparation of Cosmetic Powder Surface-Treated with Triethoxysilylethyl Polydimethylsiloxyethylhexyl Dimethicone)
12 kg of red iron oxide powder was admitted into a Henschel mixer. With stirring and mixing, 720 g of the organic solvent dispersion of silicone oil was sprayed to the powder. After the spraying, stirring and mixing was continued for achieving uniform surface treatment. During the stirring and mixing operation, the red iron oxide powder was scraped down within the Henschel mixer. The red iron oxide powder was taken out and allowed for reaction, obtaining the red iron oxide powder which was surface-treated with 3% (external value) triethoxysilylethyl polydimethylsiloxyethylhexyl dimethicone.
(Disintegration of Cosmetic Powder by Hammer Mill)
The red iron oxide powder which was surface-treated with 3% (external value) triethoxysilylethyl polydimethylsiloxyethylhexyl dimethicone was admitted into a hammer mill where the powder was disintegrated.

Example 16

(Preparation of Organic Solvent Dispersion of Silicone Oil)
A total 600 g of an organic solvent dispersion of silicone oil was obtained by mixing 300 g of triethoxysilylethyl polydimethylsiloxyethylhexyl dimethicone with 300 g of n-hexane.
(Preparation of Cosmetic Powder Surface-Treated with Triethoxysilylethyl Polydimethylsiloxyethylhexyl Dimethicone)
10 kg of yellow iron oxide powder was admitted into a Henschel mixer. With stirring and mixing, 600 g of the organic solvent dispersion of silicone oil was sprayed to the powder. After the spraying, stirring and mixing was continued for achieving uniform surface treatment. During the stirring and mixing operation, the yellow iron oxide powder was scraped down within the Henschel mixer. The yellow iron oxide powder was taken out and allowed for reaction, obtaining the yellow iron oxide powder which was surface-treated with 3% (external value) triethoxysilyl ethyl polydimethylsiloxyethylhexyl dimethicone.
(Disintegration of Cosmetic Powder by Hammer Mill)
The yellow iron oxide powder which was surface-treated with 3% (external value) triethoxysilylethyl polydimethylsiloxyethylhexyl dimethicone was admitted into a hammer mill where the powder was disintegrated.

Example 17

(Preparation of Organic Solvent Dispersion of Silicone Oil)
A total 560 g of an organic solvent dispersion of silicone oil was obtained by mixing 280 g of triethoxysilylethyl polydimethylsiloxyethylhexyl dimethicone with 280 g of n-hexane.
(Preparation of Cosmetic Powder Surface-Treated with Triethoxysilylethyl Polydimethylsiloxyethylhexyl Dimethicone)
14 kg of black iron oxide powder was admitted into a Henschel mixer. With stirring and mixing, 560 g of the organic solvent dispersion of silicone oil was sprayed to the powder. After the spraying, stirring and mixing was continued for achieving uniform surface treatment. During the stirring and mixing operation, the black iron oxide powder was scraped down within the Henschel mixer. The black iron oxide powder was taken out and allowed for reaction, obtaining the black iron oxide powder which was surface-treated with 2% (external value) triethoxysilyl ethyl polydimethylsiloxyethylhexyl dimethicone.
(Disintegration of Cosmetic Powder by Hammer Mill)
The black iron oxide powder which was surface-treated with 2% (external value) triethoxysilylethyl polydimethylsiloxyethylhexyl dimethicone was admitted into a hammer mill where the powder was disintegrated.

Example 18

(Preparation of Organic Solvent Dispersion of Silicone Oil)
A total 750 g of an organic solvent dispersion of silicone oil was obtained by mixing 375 g of triethoxysilylethyl polydimethylsiloxyethylhexyl dimethicone with 375 g of n-hexane.
(Preparation of Cosmetic Powder Surface-Treated with Triethoxysilylethyl Polydimethylsiloxyethylhexyl Dimethicone)
15 kg of white titanium oxide powder was admitted into a Henschel mixer. With stirring and mixing, 750 g of the organic solvent dispersion of silicone oil was sprayed to the powder. After the spraying, stirring and mixing was continued for achieving uniform surface treatment. During the stirring and mixing operation, the white titanium oxide powder was scraped down within the Henschel mixer. The white titanium oxide powder was taken out and allowed for reaction, obtaining the white titanium oxide powder which was surface-treated with 2.5% (external value) triethoxysilylethyl polydimethylsiloxyethylhexyl dimethicone.

(Disintegration of Cosmetic Powder by Hammer Mill)

The white titanium oxide powder which was surface-treated with 2.5% (external value) triethoxysilylethyl polydimethylsiloxyethylhexyl dimethicone was admitted into a hammer mill where the powder was disintegrated.

On the surface-treated iron oxide and titanium oxide powders obtained in Examples 15 to 18 as above, the inventive hydrophobicity measurement was carried out using a wettability tester. The inventive hydrophobicity analysis was carried out using ethanol as the lipophilic solvent. Of the results, the values of HP(10), HP(50), HP(90), HP(100), and HP(90)-HP(10) for each powder color are summarized in Table 9.

In this test, hydrophobicity was measured by the same procedure as in Test 3 except that the surface-treated iron oxide and titanium oxide powders in Table 9 were analyzed while using a water/ethanol solvent mixture containing 30% by volume of ethanol and continuously adding ethanol at 10 mL/min, and only the surface-treated yellow iron oxide powder was used in an amount of 0.02 g.

TABLE 9

|  | HP(10) | HP(50) | HP(90) | HP(90) – HP(10) | HP(100) |
|---|---|---|---|---|---|
| Red powder | | | | | |
| Example 15 | 39.1 | 46.5 | 50.9 | 11.8 | 52.9 |
| Yellow powder | | | | | |
| Example 16 | 35.8 | 45.4 | 50.9 | 15.1 | 54.6 |
| White powder | | | | | |
| Example 18 | 37.1 | 47.5 | 51.4 | 14.3 | 57.9 |

TABLE 9-continued

|  | HP(10) | HP(50) | HP(90) | HP(90) – HP(10) | HP(100) |
|---|---|---|---|---|---|
| Black powder | | | | | |
| Example 17 | 35.9 | 41.4 | 52.3 | 16.5 | 62.1 |

It is understood from the results in Table 9 that red iron oxide pigments wherein 39≤HP(50) and HP(90)-HP(10)≤18, yellow iron oxide pigments wherein 39≤HP(50) and HP(90)-HP(10)≤21, white titanium oxide pigments wherein 43≤HP(50) and HP(90)-HP(10)≤19, and black iron oxide pigments wherein 41≤HP(50) and HP(90)-HP(10)≤18, develop a high hydrophobicity when the lipophilic solvent is ethanol.

Formulation Example

Formulation Examples using Examples are given below for further illustrating the invention although the invention is not limited thereto. Blending amounts are in % by weight unless otherwise stated.

Example 19 Emulsified Liquid Foundation

An emulsified liquid foundation was prepared according to the formulation in Table 10.

Also, hydrophobic-treated coloring pigments have a hydrophobicity as shown in Table 11.

TABLE 10

|  | Ingredients | Example 19 |
|---|---|---|
| 1 | Partially crosslinked polyether-modified silicone swollen composition *1 | 3.50 |
| 2 | Partially crosslinked silicone swollen composition *2 | 5.00 |
| 3 | Alkyl-silicone branched polyether-modified silicone *3 | 2.00 |
| 4 | Dimethyldistearylammonium hectorite | 1.20 |
| 5 | Methylpolysiloxane (6 mm²/s) | 5.00 |
| 6 | Isotridecyl isononanoate | 5.00 |
| 7 | Decamethylcyclopentasiloxane | 20.85 |
| 8 | Ethylhexyl methoxycinnamate | 5.00 |
| 9 | Hybrid silicone composite powder *4 | 2.00 |
| 10 | 1,3-butylene glycol | 5.00 |
| 11 | Sodium citrate | 0.20 |
| 12 | Sodium chloride | 1.00 |
| 13 | Purified water | 34.00 |
| 14 | Silicone-modified acrylic polymer *5 | 0.25 |
| 15 | Triethoxysilylethyl polydimethylsiloxyethylhexyl dimethicone surface-treated white titanium oxide powder in Example 6 (Table 11-1) | 8.50 |
| 16 | Triethoxysilylethyl polydimethylsiloxyethylhexyl dimethicone surface-treated yellow iron oxide powder in Example 2 (Table 11-2) | 0.97 |
| 17 | Triethoxysilylethyl polydimethylsiloxyethylhexyl dimethicone surface-treated red iron oxide powder in Example 1 (Table 11-3) | 0.41 |
| 18 | Triethoxysilylethyl polydimethylsiloxyethylhexyl dimethicone surface-treated black iron oxide powder in Example 5 (Table 11-4) | 0.12 |
| Total (%) | | 100.00 |
| Viscosity (Pa · s) | | 17.3 |

*1 KSG-210 by Shin-Etsu Chemical Co., Ltd.
*2 KSG-15 by Shin-Etsu Chemical Co., Ltd.
*3 KF-6038 by Shin-Etsu Chemical Co., Ltd.
*4 KSP-101 by Shin-Etsu Chemical Co., Ltd.
*5 KP-578 by Shin-Etsu Chemical Co., Ltd.

The viscosity was measured one day after preparation using a Brookfield rotational viscometer (Model TV-10 by Toki Sangyo Co., Ltd., rotor No. 4 and speed 6 rpm).

TABLE 11

| | Ingredients | Hydrophobicity | |
|---|---|---|---|
| | | HP(50) | HP(90) − HP(10) |
| 1 | Triethoxysilylethyl polydimethylsiloxyethylhexyl dimethicone surface-treated white titanium oxide powder in Example 6 | 74.4 | 5.5 |
| 2 | Triethoxysilylethyl polydimethylsiloxyethylhexyl dimethicone surface-treated yellow iron oxide powder in Example 2 | 73.5 | 5.3 |
| 3 | Triethoxysilylethyl polydimethylsiloxyethylhexyl dimethicone surface-treated red iron oxide powder in Example 1 | 74.0 | 2.7 |
| 4 | Triethoxysilylethyl polydimethylsiloxyethylhexyl dimethicone surface-treated black iron oxide powder in Example 5 | 75.8 | 6.7 |

Preparation Method

A W/O emulsified liquid foundation was prepared by step A of mixing ingredients (14) to (18) on a roll mill until uniform, step B of mixing ingredients (1) to (9) until uniform, step C of mixing ingredients (10) to (13) until uniform, and step D of adding C to B, emulsifying, and mixing A therewith.

The foundation of Example 19 was evaluated for temperature stability, appearance change, and color difference change. The results are shown in Table 12.

TABLE 12

| | Example 19 |
|---|---|
| Temperature stability | ⊚ |
| Appearance change | unchanged |
| Color difference change | |
| ΔL* | −0.16 |
| Δa* | 0.13 |
| Δb* | 0.18 |
| ΔE* | 0.27 |

[Temperature Stability Evaluation Method]

High temperature stability: evaluated after 1-month storage in a thermostatic chamber at 50° C.
Ordinary temperature stability: evaluated after 1-month storage in a thermostatic chamber at 25° C.
Low temperature stability: evaluated after 1-month storage in a thermostatic chamber at 5° C.
<Evaluation Criterion>
Judgment was made according to the following criterion.
⊚: excellent at three of high, ordinary and low temperatures
○: good at three of high, ordinary and low temperatures (excellent ratings at two or one temperature may be included)
X: poor (discolored, strange odor, separated) at one or more of high, ordinary and low temperatures

[Appearance Change Evaluation Method]

The appearance of a foundation after 1-month storage in a thermostatic chamber at 25° C., 50° C. or 5° C. was evaluated by visual observation.

[Color Difference Change Evaluation Method]

The L*a*b* values of a foundation after one day from preparation were measured by a spectrophotometer SQ-2000 (Nippon Denshoku Industries Co., Ltd.). After 1-month storage in a thermostatic chamber at 50° C., the L*a*b* values of the foundation were measured again, from which differences were computed.

The foundation of Example 19 having the high-hydrophobicity-treated coloring pigment incorporated therein had a low viscosity, easy spread, and a non-sticky pleasant feel-on-use. As is evident from Table 12, the foundation showed good temperature stability, no appearance change, and very small color difference changes after high-temperature storage.

Example 20

An emulsified liquid foundation was prepared according to the formulation in Table 13.

Also, hydrophobic-treated powders have a hydrophobicity as shown in Table 14.

TABLE 13

| | Ingredients | Example 20 |
|---|---|---|
| 1 | Partially crosslinked polyether-modified silicone swollen composition *1 | 5.00 |
| 2 | Partially crosslinked silicone swollen composition *2 | 6.00 |
| 3 | Branched polyether-modified silicone *3 | 2.00 |
| 4 | Methylpolysiloxane (6 mm$^2$/s) | 3.00 |
| 5 | Decamethylcyclopentasiloxane | 10.60 |
| 6 | Glycerol tri-2-ethylhexanoate | 5.00 |
| 7 | Neopentyl glycol diethylhexanoate | 2.00 |
| 8 | 1,3-butylene glycol | 5.00 |
| 9 | Sodium citrate | 0.20 |
| 10 | Sodium chloride | 1.00 |
| 11 | Purified water | 49.30 |
| 12 | Silicone-modified acrylic polymer *4 | 0.90 |
| 13 | Surface-treated white titanium oxide powder (Table 14-1) | 8.50 |
| 14 | Surface-treated yellow iron oxide powder (Table 14-2) | 0.97 |
| 15 | Surface-treated red iron oxide powder (Table 14-3) | 0.41 |
| 16 | Surface-treated black iron oxide powder (Table 14-4) | 0.12 |
| | Total (%) | 100.00 |

*1 KSG-210 by Shin-Etsu Chemical Co., Ltd.
*2 KSG-15 by Shin-Etsu Chemical Co., Ltd.
*3 KF-6028P by Shin-Etsu Chemical Co., Ltd.
*4 KP-578 by Shin-Etsu Chemical Co., Ltd.

TABLE 14

| | Ingredients | Hydrophobicity | |
|---|---|---|---|
| | | HP(50) | HP(90)-HP(10) |
| 1 | Triethoxysilylethyl polydimethylsiloxyethylhexyl dimethicone surface-treated white titanium oxide powder in Example 12 | 77.1 | 3.2 |
| 2 | Triethoxysilylethyl polydimethylsiloxyethylhexyl dimethicone surface-treated yellow iron oxide powder in Example 13 | 73.2 | 10.4 |
| 3 | Triethoxysilylethyl polydimethylsiloxyethylhexyl dimethicone surface-treated red iron oxide powder in Example 11 | 72.1 | 4.2 |
| 4 | Triethoxysilylethyl polydimethylsiloxyethylhexyl dimethicone surface-treated black iron oxide powder in Example 14 | 76.0 | 6.4 |

Preparation Method

A W/O emulsified liquid foundation was prepared by step A of mixing ingredients (12) to (16) on a roll mill until uniform, step B of mixing ingredients (1) to (7) until uniform, step C of mixing ingredients (8) to (11) until uniform, and step D of adding C to B, emulsifying, and mixing A therewith.

The foundation of Example 20 was evaluated for appearance change with time.

[Appearance Change Evaluation Method]

The appearance of a foundation after 2-month storage in a thermostatic chamber at 50° C. was evaluated by visual observation.

The results are shown in Table 15.

TABLE 15

| | Example 20 |
|---|---|
| Appearance change | unchanged |

The foundation of Example 20 generated no color stripes on the side and bottom surfaces of a storage bottle, indicating excellent stability with time.

Example 21

W/O Cream Foundation
<Preparation of Cosmetic Composition>

A W/O cream foundation was prepared by step A of milling ingredients (8) to (15) on a three-roll mill into a paste, step B of mixing paste A with ingredients (1) to (7) until uniform, step C of mixing ingredients (16) to (20) until uniform, and step D of adding C to B and emulsifying.

| | | Ingredients (%) |
|---|---|---|
| 1 | Crosslinked polyether-modified silicone *1 | 3 |
| 2 | Crosslinked dimethylpolysiloxane *2 | 7 |
| 3 | Alkyl-silicone branched polyether-modified silicone *3 | 3 |
| 4 | Decamethylcyclopentasiloxane | balance |
| 5 | Ethylhexyl methoxycinnamate | 4 |
| 6 | Diethylamino hydroxybenzoyl hexyl benzoate | 1 |
| 7 | Organo-modified clay mineral | 1.2 |
| 8 | Silicone branched polyglycerol-modified silicone *4 | 1.5 |
| 9 | Methylphenylpolysiloxane *5 | 10 |
| 10 | Isotri decyl isononanoate | 7 |
| 11 | Surface-treated white titanium oxide powder *6 | 8.5 |
| 12 | Surface-treated yellow iron oxide powder *6 | 1 |
| 13 | Surface-treated red iron oxide powder *6 | 0.4 |
| 14 | Surface-treated black iron oxide powder *6 | 0.1 |
| 15 | Metal soap-treated superfine titanium oxide | 10 |
| 16 | Dipropylene glycol | 5 |
| 17 | Phenoxyethanol | 0.2 |
| 18 | Sodium citrate | appropriate |
| 19 | Magnesium sulfate | appropriate |
| 20 | Purified water | 30 |
| | Total | 100.0% |

*1 KSG-240 by Shin-Etsu Chemical Co., Ltd.
*2 KSG-15 by Shin-Etsu Chemical Co., Ltd.
*3 KF-6038 by Shin-Etsu Chemical Co., Ltd.
*4 KF-6106 by Shin-Etsu Chemical Co., Ltd.
*5 KF-56A by Shin-Etsu Chemical Co., Ltd.
*6 surface-treated powders used in Example 19 (Examples 1, 2, 5, 6; Table 11)

The cream foundation shows easy spread, pleasant feel-on-use, no spoiling, and high stability with time.

Example 22

Powder Foundation
<Preparation of Cosmetic Composition>

A powder foundation was prepared by step A of mixing ingredients (1) to (3) until uniform, step B of mixing ingredients (4) to (12) until uniform, step C of adding A to B and mixing on a Henschel mixer until uniform. The resulting powder was passed through a mesh screen and pressed in a metal case by a punch.

| | | Ingredients (%) |
|---|---|---|
| 1 | 2-ethylhexyl p-methoxycinnamate | 4 |
| 2 | Diphenylsiloxyphenyl trimethicone *1 | 4.5 |
| 3 | Triethylhexanoin | 1.5 |
| 4 | Barium sulfate | 10 |
| 5 | Phenyl-modified hybrid silicone composite powder *2 | 5 |
| 6 | Polymethylsilsesquioxane *3 | 4 |
| 7 | Alkyl-silicone branched silicone-treated mica *4 | 30 |
| 8 | Alkyl-silicone branched silicone-treated talc *4 | 33.3 |
| 9 | Surface-treated white titanium oxide powder *5 | 6 |
| 10 | Surface-treated yellow iron oxide powder *5 | 1.0 |
| 11 | Surface-treated red iron oxide powder *5 | 0.5 |
| 12 | Surface-treated black iron oxide powder *5 | 0.2 |
| | Total | 100.0% |

*1 KF-56A by Shin-Etsu Chemical Co., Ltd.
*2 KSP-300 by Shin-Etsu Chemical Co., Ltd.
*3 KMP-590 by Shin-Etsu Chemical Co., Ltd.
*4 treated with KF-9909 by Shin-Etsu Chemical Co., Ltd.
*5 surface-treated powders used in Example 19 (Examples 1, 2, 5, 6; Table 11)

The powder foundation showed fine texture, light spread, and good adhesion.

Example 23

Lipstick
<Preparation of Cosmetic Composition>

A lipstick was prepared by step A of heating ingredients (1) to (6) at 95° C. and mixing until uniform, step B of adding ingredients (7) to (9) thereto, heating at 70° C., and mixing until uniform, step C of adding ingredients (10) to (17) to B on a three-roll mill, heating at 70° C., and mixing until uniform, and thereafter cooling to room temperature.

|   | Ingredients | (%) |
|---|---|---|
| 1 | Candelilla wax | 8.6 |
| 2 | Polyethylene | 5 |
| 3 | Microcrystalline wax | 0.8 |
| 4 | Silicone wax *1 | 8.2 |
| 5 | Macadamia nut oil | 6.6 |
| 6 | Isotridecyl isononanoate | 4.5 |
| 7 | Acrylic silicone base graft copolymer *2 | 40 |
| 8 | Silicone branched polyglycerol-modified silicone *3 | 0.5 |
| 9 | Decamethylcyclopentasiloxane | balance |
| 10 | Diisostrearyl malonate | 6 |
| 11 | Red #201 | 0.3 |
| 12 | Red #202 | 0.4 |
| 13 | Yellow #4 | 1.2 |
| 14 | Surface-treated white titanium oxide powder *4 | 2.9 |
| 15 | Surface-treated black iron oxide powder *4 | 0.2 |
| 16 | Surface-treated red iron oxide powder *4 | 0.7 |
| 17 | Mica | 7.3 |
|   | Total | 100.0% |

*1 KP-561P by Shin-Etsu Chemical Co., Ltd.
*2 KP-545 by Shin-Etsu Chemical Co., Ltd.
*3 KF-6106 by Shin-Etsu Chemical Co., Ltd.
*4 surface-treated powders used in Example 20 (Examples 12, 14, 11; Table 14)

The lipstick showed neither color stripes nor unevenness, good color development, pleasant feel-on-use, and good color retention.

Example 24

Non-Aqueous Concealer
<Preparation of Cosmetic Composition>
A non-aqueous concealer was prepared by step A of milling ingredients (7) to (12) on a three-roll mill into a paste and step B of mixing A and ingredients (1) to (6) until uniform.

|   | Ingredients | (%) |
|---|---|---|
| 1 | Hybrid silicone composite powder *1 | 23 |
| 2 | Phenyl-modified hybrid silicone composite powder *2 | 5 |
| 3 | Crosslinked dimethylpolysiloxane *3 | 6 |
| 4 | Dimethylpolysiloxane (6 cs) | 40 |
| 5 | Methylphenylpolysiloxane *4 | 7 |
| 6 | Decamethylcyclopentasiloxane | 12.9 |
| 7 | Triethylhexanoin | 0.2 |
| 8 | Silicone branched polyether-modified silicone *5 | 0.5 |
| 9 | Surface-treated white titanium oxide powder *6 | 5 |
| 10 | Surface-treated yellow iron oxide powder *6 | 0.25 |
| 11 | Surface-treated red iron oxide powder *6 | 0.1 |
| 12 | Surface-treated black iron oxide powder *6 | 0.05 |
|   | Total | 100.0% |

*1 KSP-101 by Shin-Etsu Chemical Co., Ltd.
*2 KSP-300 by Shin-Etsu Chemical Co., Ltd.
*3 KSG-19 by Shin-Etsu Chemical Co., Ltd.
*4 KF-56A by Shin-Etsu Chemical Co., Ltd.
*5 KF-6028P by Shin-Etsu Chemical Co., Ltd.
*6 surface-treated powders used in Example 19 (Examples 1, 2, 5, 6; Table 11)

The concealer showed easy spread and good adhesion as powder, light touch, and good stability with time.

Example 25

O/W Cream
<Preparation of Cosmetic Composition>
A cream was prepared by step A of mixing ingredients (3) to (10) and step B of mixing ingredients (1) and (2), adding A thereto, and stirring for emulsification.

|   | Ingredients | (%) |
|---|---|---|
| 1 | Crosslinked dimethylpolysiloxane *1 | 10.0 |
| 2 | Glyceryl triethylhexanoate | 5.0 |
| 3 | Dipropylene glycol | 7.0 |
| 4 | Glycerin | 5.0 |
| 5 | Methyl cellulose (2% aqueous solution) *2 | 7.0 |
| 6 | Polyacrylamide base emulsifier *3 | 2.0 |
| 7 | Surface-treated white titanium oxide powder *4 | 1.0 |
| 8 | Preservative | appropriate |
| 9 | Perfume | appropriate |
| 10 | Purified water | balance |
|   | Total | 100.0% |

*1 KSG-16 by Shin-Etsu Chemical Co., Ltd.
*2 Metolose SM-4000 by Shin-Etsu Chemical Co., Ltd.
*3 Sepigel 305 by SEPPIC
*4 surface-treated white titanium oxide powder in Example 6, hydrophobicity HP(50) = 74.4, HP(90)-HP(10) = 5.5

The cream showed light spread, non-stickiness, fresh feel-on-use, and good stability with time.

Example 26

W/O Mascara
<Preparation of Cosmetic Composition>
A W/O mascara was prepared by step A of heating ingredients (1) to (8) at 95° C. and mixing them until uniform, step B of heating A and ingredients (9) to (14) at 85° C. and mixing until uniform, step C of heating ingredients (15) to (17) at 85° C. and mixing them until uniform, and step D of adding C to B, emulsifying, and slowly cooling.

|   | Ingredients | (%) |
|---|---|---|
| 1 | Trimethylsiloxysilicic acid in isododecane *1 | 10 |
| 2 | Acrylic-silicone graft copolymer in isododecane *2 | 10 |
| 3 | Dextrin Palmitate/ethylhexanoate *3 | 3 |
| 4 | Silicone wax *4 | 2 |
| 5 | Ceresin | 2.5 |
| 6 | Beeswax | 4.5 |
| 7 | Diphenylsiloxyphenyl dimethicone *5 | 3 |
| 8 | Isododecane | balance |
| 9 | Organo-modified clay mineral | 4 |
| 10 | Surface-treated black iron oxide powder *6 | 5 |
| 11 | Alkyl-silicone branched silicone-treated talc *7 | 4.5 |
| 12 | Silicone branched polyether-modified silicone *8 | 1 |
| 13 | Propylene carbonate | 1.3 |
| 14 | Phenoxyethanol | 0.2 |
| 15 | 1,3-butylene glycol | 1 |
| 16 | Purified water | 12.8 |
|   | Total | 100.0% |

*1 X-21-5595 by Shin-Etsu Chemical Co., Ltd.
*2 KP-550 by Shin-Etsu Chemical Co., Ltd.
*3 Rheopearl TT2 by Chiba Flour Milling Co., Ltd.
*4 KP-562P by Shin-Etsu Chemical Co., Ltd.
*5 KF-56A by Shin-Etsu Chemical Co., Ltd.
*6 surface treated powder used in Example 5
*7 treated with KF-9909 by Shin-Etsu Chemical Co., Ltd.
*8 KF-6028 by Shin-Etsu Chemical Co., Ltd.

The W/O mascara showed non-lumpiness, long lasting, and good retention.

Example 27

W/O Cream Foundation
<Preparation of Cosmetic Composition>

A W/O cream foundation was prepared by step A of milling ingredients (8) to (15) on a three-roll mil into a paste, step B of mixing A with ingredients (1) to (7) until uniform, step C of mixing ingredients (16) to (20) until uniform, and step D of adding C to B and emulsifying.

|    |                                                    | Ingredients (%) |
|----|----------------------------------------------------|-----------------|
| 1  | Crosslinked polyether-modified silicone *1         | 3               |
| 2  | Crosslinked dimethylpolysiloxane *2                | 5               |
| 3  | Alkyl-silicone branched polyether-modified silicone *3 | 3           |
| 4  | Decamethylcyclopentasiloxane                       | 8.4             |
| 5  | Ethylhexyl methoxycinnamate                        | 4               |
| 6  | Diethylamino hydroxybenzoyl hexyl benzoate         | 1               |
| 7  | Organo-modified bentonite                          | 1.2             |
| 8  | Silicone branched polyglycerin-modified silicone *4 | 1.5            |
| 9  | Methylphenylpolysiloxane *5                        | 10              |
| 10 | Isotridecyl isononanoate                           | 7               |
| 11 | Surface-treated white titanium oxide powder *6     | 8.5             |
| 12 | Surface-treated yellow iron oxide powder *7        | 1               |
| 13 | Surface-treated red iron oxide powder *8           | 0.4             |
| 14 | Surface-treated black iron oxide powder *9         | 0.1             |
| 15 | Metal soap-treated superfine titanium oxide        | 10              |
| 16 | Dipropylene glycol                                 | 5               |
| 17 | Phenoxyethanol                                     | 0.2             |
| 18 | Sodium citrate                                     | 0.2             |
| 19 | Magnesium sulfate                                  | 0.5             |
| 20 | Purified water                                     | 30              |
|    | Total                                              | 100.0%          |

*1 KSG-240 by Shin-Etsu Chemical Co., Ltd.
*2 KSG-15 by Shin-Etsu Chemical Co., Ltd.
*3 KF-6038 by Shin-Etsu Chemical Co., Ltd.
*4 KF-6106 by Shin-Etsu Chemical Co., Ltd.
*5 KF-56A by Shin-Etsu Chemical Co., Ltd.
*6 surface-treated white titanium oxide powder in Example 18
*7 surface-treated yellow iron oxide powder in Example 16
*8 surface-treated red iron oxide powder in Example 15
*9 surface-treated black iron oxide powder in Example 17

The cream foundation shows easy spread, pleasant feel-on-use, no fading, and high stability with time.

Example 28

Powder Foundation
<Preparation of Cosmetic Composition>

A powder foundation was prepared by step A of mixing ingredients (1) to (3) until uniform, step B of mixing ingredients (4) to (14) until uniform, step C of adding A to B and mixing them on a Henschel mixer until uniform. The resulting powder was passed through a mesh screen and pressed in a metal case by a punch.

|    |                                                    | Ingredients (%) |
|----|----------------------------------------------------|-----------------|
| 1  | 2-ethylhexyl p-methoxycinnamate                    | 4.5             |
| 2  | Macadamia nut oil                                  | 2               |
| 3  | Sorbitan sesquiisostearate                         | 0.25            |
| 4  | Polyethylene powder                                | 1.5             |
| 5  | Barium sulfate                                     | 11.0            |
| 6  | Hybrid silicone composite powder *1                | 4               |
| 7  | Polymethylsilsesquioxane *2                        | 3               |
| 8  | Metal soap-treated superfine titanium oxide        | 7               |
| 9  | Alkyl-silicone branched silicone-treated mica *3   | 28              |
| 10 | Alkyl-silicone branched silicone-treated talc *3   | 32.75           |
| 11 | Surface-treated white titanium oxide powder *4     | 4               |
| 12 | Surface-treated yellow iron oxide powder *5        | 1.2             |
| 13 | Surface-treated red iron oxide powder *6           | 0.6             |
| 14 | Surface-treated black iron oxide powder *7         | 0.2             |
|    | Total                                              | 100.0%          |

*1 KSP-441 by Shin-Etsu Chemical Co., Ltd.
*2 KMP-591 by Shin-Etsu Chemical Co., Ltd.
*3 treated with KF-9909 by Shin-Etsu Chemical Co., Ltd.
*4 surface-treated white titanium oxide powder in Example 18
*5 surface-treated yellow iron oxide powder in Example 16
*6 surface-treated red iron oxide powder in Example 15
*7 surface-treated black iron oxide powder in Example 17

The powder foundation showed fine texture, light spread, and good adhesion.

Example 29

Lipstick
<Preparation of Cosmetic Composition>

A lipstick was prepared by step A of heating ingredients (1) to (8) at 95° C. and mixing until uniform, step B of dispersing ingredients (9) to (14), part of (4), and (15) in A on a three-roll mill, heating at 95° C., and mixing until uniform. The resulting composition was cast into a mold and cooled.

|    |                                                    | Ingredients (%) |
|----|----------------------------------------------------|-----------------|
| 1  | Polyethylene                                       | 7               |
| 2  | Microcrystalline wax                               | 3               |
| 3  | Silicone wax *1                                    | 10.5            |
| 4  | Triethylhexanoin                                   | 19.3            |
| 5  | Neopentylglycol diethylhexanoate                   | 15              |
| 6  | Neopentylglycol dicaprate                          | 7               |
| 7  | Hydrogenated polyisobutene                         | 20              |
| 8  | Diphenyl dimethicone *2                            | 7.5             |
| 9  | Red #201                                           | 0.3             |
| 10 | Red #202                                           | 0.4             |
| 11 | Yellow #4 Al Lake                                  | 1.2             |
| 12 | Surface-treated white titanium oxide powder *3     | 2.9             |
| 13 | Surface-treated black iron oxide powder *4         | 0.2             |
| 14 | Surface-treated red iron oxide powder *5           | 0.7             |
| 15 | Mica titanium                                      | 5.0             |
|    | Total                                              | 100.0%          |

*1 KP-561P by Shin-Etsu Chemical Co., Ltd.
*2 KF-54HV by Shin-Etsu Chemical Co., Ltd.
*3 surface-treated white titanium oxide powder in Example 18
*4 surface-treated black iron oxide powder in Example 17
*5 surface-treated red iron oxide powder in Example 15

The lipstick showed neither color stripes nor unevenness, good color development, pleasant feel-on-use, and good color retention.

Example 30

Non-Aqueous Concealer
<Preparation of Cosmetic Composition>

A non-aqueous concealer was prepared by step A of milling ingredients (7) to (12) on a three-roll mill into a paste and step B of mixing A and ingredients (1) to (6) until uniform.

|   | Ingredients | (%) |
|---|---|---|
| 1 | Hybrid silicone composite powder *1 | 20 |
| 2 | Phenyl-modified hybrid silicone composite powder *2 | 8 |
| 3 | Crosslinked dimethylpolysiloxane *3 | 6 |
| 4 | Dimethylpolysiloxane (6 cs) | 40 |
| 5 | Methylphenylpolysiloxane *4 | 7 |
| 6 | Decamethylcyclopentasiloxane | 12.9 |
| 7 | Triethylhexanoin | 0.2 |
| 8 | Silicone branched polyether-modified silicone *5 | 0.5 |
| 9 | Surface-treated white titanium oxide powder *6 | 5 |
| 10 | Surface-treated yellow iron oxide powder *7 | 0.25 |
| 11 | Surface-treated red iron oxide powder *8 | 0.1 |
| 12 | Surface-treated black iron oxide powder *9 | 0.05 |
|   | Total | 100.0% |

*1 KSP-100 by Shin-Etsu Chemical Co., Ltd.
*2 KSP-300 by Shin-Etsu Chemical Co., Ltd.
*3 KSG-16 by Shin-Etsu Chemical Co., Ltd.
*4 KF-56A by Shin-Etsu Chemical Co., Ltd.
*5 KF-6028P by Shin-Etsu Chemical Co., Ltd.
*6 surface-treated white titanium oxide powder in Example 18
*7 surface-treated yellow iron oxide powder in Example 16
*8 surface-treated red iron oxide powder in Example 15
*9 surface-treated black iron oxide powder in Example 17

The concealer showed easy spread and good adhesion, light touch, and good stability with time.

Example 31

O/W Cream
<Preparation of Cosmetic Composition>

A cream was prepared by step A of mixing ingredients (3) to (10) and step B of mixing ingredients (1) and (2), adding A thereto, and stirring for emulsification.

|   | Ingredients | (%) |
|---|---|---|
| 1 | Crosslinked dimethylpolysiloxane *1 | 10.0 |
| 2 | Glyceryl triethylhexanoate | 5.0 |
| 3 | Dipropylene glycol | 7.0 |
| 4 | Glycerin | 5.0 |
| 5 | Methyl cellulose (2% aqueous solution) *2 | 7.0 |
| 6 | Polyacrylamide base emulsifier *3 | 2.0 |
| 7 | Surface-treated white titanium oxide powder *4 | 1.0 |
| 8 | Preservative | 0.3 |
| 9 | Perfume | 0.2 |
| 10 | Purified water | 62.5 |
|   | Total | 100.0% |

*1 KSG-16 by Shin-Etsu Chemical Co., Ltd.
*2 Metolose SM-4000 by Shin-Etsu Chemical Co., Ltd.
*3 Sepigel 305 by SEPPIC
*4 surface-treated white titanium oxide powder in Example 18

The cream showed light spread, non-stickiness, fresh feel-on-use, and good stability with time.

Example 32

W/O Mascara
<Preparation of Cosmetic Composition>

A W/O mascara was prepared by step A of heating ingredients (1) to (8) at 95° C. and mixing them until uniform, step B of heating A and ingredients (9) to (14) at 85° C. and mixing until uniform, step C of heating ingredients (15) to (16) at 85° C. and mixing until uniform, and step D of adding C to B, emulsifying, and slowly cooling.

|   | Ingredients | (%) |
|---|---|---|
| 1 | Trimethylsiloxysilicic acid in isododecane *1 | 12 |
| 2 | Acrylic-silicone graft copolymer in isododecane *2 | 12 |
| 3 | Dextrin palmitate/ethylhexanoate *3 | 3 |
| 4 | Silicone wax *4 | 2 |
| 5 | Ceresin | 2.5 |
| 6 | Beeswax | 4.5 |
| 7 | Diphenylsiloxyphenyl dimethicone *5 | 3 |
| 8 | Isododecane | 31.2 |
| 9 | Organo-modified bentonite | 4 |
| 10 | Surface-treated black iron oxide powder *6 | 5 |
| 11 | Alkyl-silicone branched silicone-treated talc *7 | 4.5 |
| 12 | Silicone branched polyether-modified silicone *8 | 1 |
| 13 | Propylene carbonate | 1.3 |
| 14 | Phenoxyethanol | 0.2 |
| 15 | 1,3-butylene glycol | 1 |
| 16 | Purified water | 12.8 |
|   | Total | 100.0% |

*1 X-21-5595 by Shin-Etsu Chemical Co., Ltd.
*2 KP-550 by Shin-Etsu Chemical Co., Ltd.
*3 Rheopearl TT2 by Chiba Flour Milling Co., Ltd.
*4 KP-562P by Shin-Etsu Chemical Co., Ltd.
*5 KF-56A by Shin-Etsu Chemical Co., Ltd.
*6 surface-treated black iron oxide powder in Example 17
*7 treated with KF-9909 by Shin-Etsu Chemical Co., Ltd.
*8 KF-6028 by Shin-Etsu Chemical Co., Ltd.

The W/O mascara showed non-lumpiness, long lasting, and good retention.

The invention claimed is:

1. A method for analyzing the degree of hydrophobicity of a powder, comprising:
adding a sample powder to be evaluated for its degree of hydrophobicity to a solvent mixture of a lipophilic solvent and a hydrophilic solvent,
continuously adding the lipophilic solvent to the solvent mixture having the powder added thereto,
measuring a voltage rate of the solvent mixture at predetermined time intervals, at least until the voltage rate reaches the minimum,
provided that for data discrete values as measured, the voltage rate observed relative to time series $t_i$ (wherein i is an integer, $t_i < t_{i+1}$) is $R_i$, the maximum of voltage rate is 100, and the minimum of voltage rate is $R_{min}$, a parameter correlating to a powder concentration relative to an arbitrary voltage rate R in the range: $R_{min} < R < 100$ is defined as

[Math. 1]
$$x = \frac{100 - R}{100 - R_{min}} \times 100 \text{ (wherein } 0 < x < 100\text{),}$$

a lipophilic solvent ratio in the solvent mixture corresponding to that x is represented by HP(x), a continuous function HP(x) of lipophilic solvent ratio is defined, for R meeting the range: $R_{i+1} \leq R < R_i$ wherein i is an integer, as

[Math. 2]
$$HP(x) = \frac{HP_{i+1} - HP_i}{R_{i+1} - R_i} \times (R - R_i) + HP_i,$$

and the parameter x (wherein 0<x<100) changes in proportion to a powder concentration c(t) (wherein $0 < c(t) < c_{max}$) or cumulative sedimentation weight W(t) (wherein 0<W(t)<

$W_{max}$), computing HP(x) at a preselected value of x as a representative value of the lipophilic solvent ratio distribution, the HP(x) being regarded as an index of hydrophobicity.

2. The analysis method of claim 1 wherein for the voltage rate $R_i$ observed relative to time series $t_i$, measurement data at total (2n+1) points (wherein n is an integer) including a certain point and fore and aft n points are averaged, a value obtained by smoothening according to the equation:

[Math. 3]
$$\overline{R_i} = \sum_{i=-n}^{n} R_i$$

is used as the voltage rate, the maximum of voltage rate is 100, and the minimum of averaged voltage rate is $$\overline{R_{min}},$$ [Math. 4]

a parameter correlating to a powder concentration with respect to an arbitrary voltage rate R in the range:

$$\overline{R_{min}} < R < 100$$ [Math. 5]

is defined as

[Math. 6]
$$x = \frac{100 - R}{100 - \overline{R_{min}}} \times 100 \text{ (wherein } 0 < x < 100\text{)},$$

a lipophilic solvent ratio corresponding to that x is represented by HP(x),
for R meeting the range:

$$\overline{R_{i+1}} \leq R < \overline{R_i}$$ [Math. 7]

a continuous function HP(x) of lipophilic solvent ratio is defined as

[Math. 8]
$$HP(x) = \frac{HP_{i+1} - HP_i}{\overline{R_{i+1}} - \overline{R_i}} \times (R - \overline{R_i}) + HP_i.$$

3. The analysis method of claim 1 wherein HP(50) is computed as a representative value of the lipophilic solvent ratio distribution.

4. The analysis method of claim 3 wherein when the lipophilic solvent is methanol and the hydrophilic solvent is water, a powder having a parameter HP(50) meeting 68.0≤HP(50) is evaluated as having a high degree of hydrophobicity.

5. The analysis method of claim 4 wherein when HP(10) and HP(90) are further computed, and HP(90)-HP(10) is used as an index for variation of the lipophilic solvent ratio, a powder meeting HP(90)-HP(10)≤22.0 is evaluated as having a small variation.

6. A method for evaluating a hydrophobic-treated pigment comprising analyzing an inorganic pigment which has been subjected to hydrophobic surface treatment by the hydrophobicity analysis method of claim 5,
a red iron oxide pigment meeting 68.0≤HP(50) and HP(90)-HP(10)≤16.0,
a yellow iron oxide pigment meeting 68.0≤HP(50) and HP(90)-HP(10)≤22.0,
a white titanium oxide pigment meeting 73.0≤HP(50) and HP(90)-HP(10)≤20.0 or
a black iron oxide pigment meeting 72.5≤HP(50) and HP(90)-HP(10)≤9.0,
being evaluated as having a small variation and a high degree of hydrophobicity.

7. A method for evaluating a hydrophobic-treated pigment comprising analyzing a coloring pigment which has been subjected to hydrophobic surface treatment by the hydrophobicity analysis method of claim 4, a pigment meeting 68.0≤HP(50) being evaluated as having a high degree of hydrophobicity.

8. The evaluating method of claim 7 wherein the hydrophobic surface treatment is a surface treatment with a silicone compound as at least one treating agent.

9. A method for evaluating a hydrophobic-treated pigment comprising analyzing an inorganic pigment which has been subjected to hydrophobic surface treatment by the hydrophobicity analysis method of claim 4,
a red iron oxide pigment meeting 68.0≤HP(50),
a yellow iron oxide pigment meeting 68.0≤HP(50),
a white titanium oxide pigment meeting 73.0≤HP(50) or
a black iron oxide pigment meeting 72.5≤HP(50),
being evaluated as having a high degree of hydrophobicity.

10. The analysis method of claim 3 wherein when the lipophilic solvent is ethanol and the hydrophilic solvent is water, a powder having a parameter HP(50) meeting 30.0≤HP(50) is evaluated as having a high degree of hydrophobicity.

11. The analysis method of claim 10 wherein when HP(10) and HP(90) are further computed, and HP(90)-HP(10) is used as a measure for variation of the lipophilic solvent ratio, a powder meeting HP(90)-HP(10)≤28.0 is evaluated as having a small variation.

12. A method for evaluating a hydrophobic-treated pigment comprising analyzing an inorganic pigment which has been subjected to hydrophobic surface treatment by the hydrophobicity analysis method of claim 11,
a red iron oxide pigment meeting 30.0≤HP(50) and HP(90)-HP(10)≤18.0,
a yellow iron oxide pigment meeting 30.0≤HP(50) and HP(90)-HP(10)≤21.0,
a white titanium oxide pigment meeting 36.0≤HP(50) and HP(90)-HP(10)≤19.0 or
a black iron oxide pigment meeting 40.0≤HP(50) and HP(90)-HP(10)≤18.0,
being evaluated as having a small variation and a high degree of hydrophobicity.

13. A method for evaluating a hydrophobic-treated pigment comprising analyzing a coloring pigment which has been subjected to hydrophobic surface treatment by the hydrophobicity analysis method of claim 10, a pigment meeting 30.0≤HP(50) being evaluated as having a high degree of hydrophobicity.

14. A method for evaluating a hydrophobic-treated pigment comprising analyzing an inorganic pigment which has been subjected to hydrophobic surface treatment by the hydrophobicity analysis method of claim 10,
a red iron oxide pigment meeting 30.0≤HP(50),
a yellow iron oxide pigment meeting 30.0≤HP(50),
a white titanium oxide pigment meeting 36.0≤HP(50) or
a black iron oxide pigment meeting 40.0≤HP(50),
being evaluated as having a high degree of hydrophobicity.

15. The analysis method of claim 1 wherein the lipophilic solvent is at least one solvent selected from methanol, ethanol, isopropyl alcohol, butyl alcohol, and acetone, and the hydrophilic solvent is water.

* * * * *